US005384260A

United States Patent [19]
Osborne et al.

[11] Patent Number: 5,384,260
[45] Date of Patent: * Jan. 24, 1995

[54] DETECTION OF ONSET OF ANTIESTROGEN RESISTANCE IN BREAST CANCER

[75] Inventors: C. Kent Osborne; Michael W. DeGregorio, both of San Antonio, Tex.

[73] Assignees: Board of Regents, The University of Texas System, Austin, Tex.; Yale University, New Haven, Conn.

[*] Notice: The portion of the term of this patent subsequent to Jun. 9, 2009 has been disclaimed.

[21] Appl. No.: 30,351

[22] Filed: Mar. 17, 1993

Related U.S. Application Data

[63] Continuation-in-part of Ser. No. 577,790, Sep. 5, 1990, Pat. No. 5,119,827.

[51] Int. Cl.$^6$ .......................... G01N 33/48
[52] U.S. Cl. .......................... 436/64; 435/4; 435/32; 424/9; 128/749; 128/898
[58] Field of Search .......................... 436/64; 435/4, 32; 424/9; 128/749, 898; 604/48, 49, 50, 51

[56] References Cited

U.S. PATENT DOCUMENTS

| | | | |
|---|---|---|---|
| 4,806,464 | 2/1989 | Spelsberg | 435/6 |
| 4,919,937 | 4/1990 | Mauvais-Jarvis et al. | 424/449 |
| 5,023,234 | 6/1991 | Labrie | 514/15 |
| 5,030,417 | 7/1991 | Spelsberg | 422/61 |
| 5,119,827 | 6/1992 | Osborne et al. | 128/749 |

FOREIGN PATENT DOCUMENTS

| | | |
|---|---|---|
| 0272791A2 | 6/1988 | European Pat. Off. . |
| WO89/01153 | 2/1989 | WIPO . |
| PCT/US91/-06323 | 12/1991 | WIPO . |
| WO92/03973 | 3/1992 | WIPO . |

OTHER PUBLICATIONS

Armstrong et al., "Separation of tamoxifen geometric isomers and metabolites by bonded-phase β-cyclodextrin chromatography," *Journal of Chromatograpy*, (1987) 414:192–196, published in Europe.

Katzenellenbogen et al., "Facile Geometric Isomerization of Phenolic Non-Steroidal Estrogens and Antiestrogens: Limitations to the Interpretation of Experiments Characterizing The Activity of Individual Isomers," *J. Steroid Biochem.*, (1985) 22(5):589–596, published in Europe.

Katzenellenbogen et al., "Bioactivities, Estrogen Receptor Interactions, and Plasminogen Activator-inducing Activities of Tamoxifen and Hydroxytamoxifen Isomers in MCF-7 Human Breast Cancer Cells," *Cancer Research*, (1984) 44:112–119, published in the U.S.A.

Robertson et al., "Tamoxifen Antiestrogens. A Comparison of the Activity, Pharmacokinetics, and Metabolic Activation of the *Cis* and *Trans* Isomers of Tamoxifen," *J. Steroid Biochem.* (1982) 16:1–13, published in Europe.

Jordan, et al., "Geometric Isomers of Substituted Triphenylethylenes and Antiestrogen Action," *Endocrinology* (1981) 108(4):1353–1361, published in U.S.A.

(List continued on next page.)

Primary Examiner—James C. Housel
Assistant Examiner—Maureen M. Wallen
Attorney, Agent, or Firm—Arnold, White & Durkee

[57] ABSTRACT

The present invention involves a method for early detection of developing tamoxifen resistance in breast cancer. Tamoxifen is the drug of choice for hormonal therapy of a first recurrence of breast cancer, but its use is associated eventually with emergence of resistant tumors. Whereas initial treatment is usually followed by tumor regression, resistant tumors may actually resume growth under continued tamoxifen treatment. Because such growth may actually be augmented by the tamoxifen, it is essential to identify the onset of resistance as early as possible so alternative therapy may be promptly instituted. Monitoring increased levels of estrogenic tamoxifen isomers or estrogenic tamoxifen metabolites signals developing resistance.

21 Claims, 18 Drawing Sheets

OTHER PUBLICATIONS

V. C. Jordan, "Antiestrogenic and Antitumor Properties of Tamoxifen in Laboratory Animals," *Cancer Treatment Reports* (1976) 60(10):1409–1419, published in the U.S.A.

Fromson, et al., "The Matabolism of Tamoxifen* (I.C.I. 46, 474) Part II: In Female Patients," *Xenobiotica* (1973) 3(11):711–714, published in Europe.

Fromson, et al., "The Metabolism of Tamoxifen* (I.C.I. 46, 474) Part I: In Laboratory Animals," *Xenobiotica* (1973) 3(11):693–709, published in Europe.

L. Terenius, "Structure–Activity Relationships of Anti-–Oestrogens With Regard To Interaction With 17$\beta$–O-estradiol In The Mouse Uterus And Vagina," *Acta Endocrinologica* (1971) 66:431–447, published in Europe.

Harper and Walpole, "A New Derivative of Triphenylethylene: Effect on Implantation and Mode of Action in Rats," *J. Reprod. Fert.* (1967) 13:101–119, published in Europe.

Medline Search Report, (1990), printed in U.S.A.

Dialog Search Report, (1990), printed in U.S.A.

Murphy et al., "Structure–Function Relationships of Hydroxylated Metabolites of Tamoxifen that Control the Proliferation of Estrogen–Responsive T47D Breast Cancer Cells In Vitro", *Mole. Pharm.* (1990) 38:737–743, published in U.S.A.

Simon et al., "Development of Resistance To Tamoxifen And Progestins In Human Mammary Cancer," *Proc. Int. Congr. Chemuther.* (1983) 18:270/1–4, published in U.S.A.

Jordan et al., "Ligand Interaction at the Estrogen Receptor to Program Antiestrogen Action: A Study With Nonsteroidal Compounds in Vitro*," *Endocrinology* (1988) 122(4):1449–1454, published in U.S.A.

Jordan et al., "Ligand Interaction at the Estrogen Receptor to Program Antiestrogen Action: A Study with Nonsteroidal Compounds In Vitro," *Chemical Abstracts*, (1988) 108:198501d, published in U.S.A.

Jordan et al., "Ligand Interaction at the Estrogen Receptor to Program Antiestrogen Action: A Study with Nonsteroidal Compounds In Vitro," *Dialog* Printout, (1991), printed in USA.

Murphy et al., "Structure–Function Relationships of Hydroxylated Metabolites of Tamoxifen that Control the Proliferation of Estrogen–Responsive T47D Breast Cancer Cells In Vitro", *Dialog* Printout (1991), printed in U.S.A.

Murphy et al., "Structure–Function Relationships of Hydroxylated Metabolites of Tamoxifen that Control the Proliferation of Estrogen–Responsive T47D Breast Cancer Cells In Vitro", *Chemical Abstracts (1991) 114:55296d, published in U.S.A.*

Jordan et al., "Resistance to Antiestrogen Therapy" in Drug Resistance, D. Kessle (ed.), CRC Press, Boca Raton, Fla., 1987, pp. 403–427.

Sensitive (1) and Resistant (2) MCF-7 Tumors:

Trans

Cis

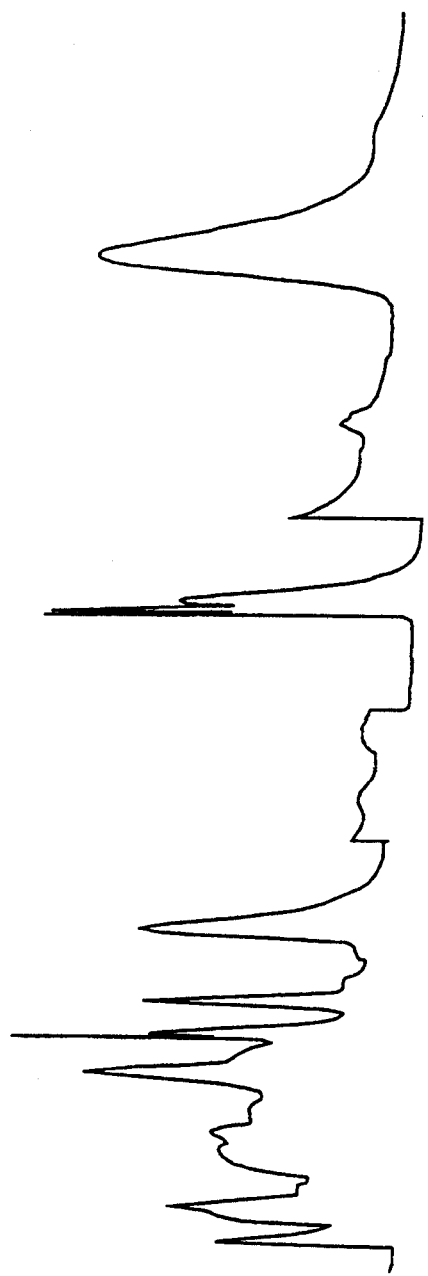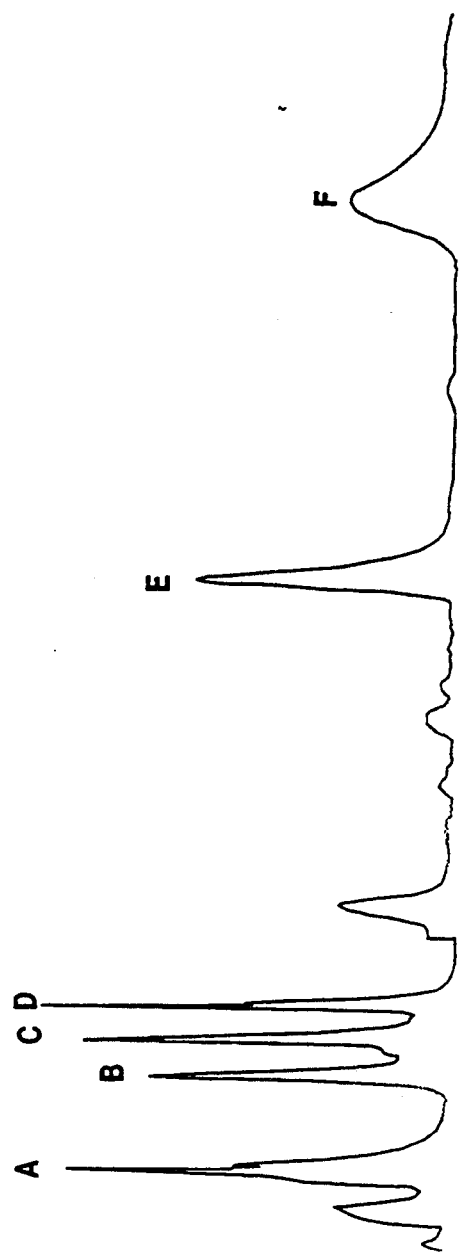

DETECTION OF ONSET OF ANTIESTROGEN RESISTANCE IN BREAST CANCER

The instant application is the U.S. filing of PCT/US91/06323, which is a continuation-in-part of U.S. Ser. No. 07/577,790 filed Sep. 5, 1990 and now issued as U.S. Pat. No. 5,119,827 on Jun. 9, 1992.

The present invention relates to methods for monitoring the effectiveness of tamoxifen (2-[4-(1,2-diphenyl-1-butenyl)phenoxy]-N,N-dimethylethanamine) therapy in the treatment of breast cancer, and more particularly to methods of detecting the emergence of tamoxifen-resistant tumors and the resulting treatment resistance by means of analytical assays for antiestrogenic and other forms of tamoxifen as well as its estrogenic metabolites.

Breast cancer is the most common form of malignant disease among women of the Western world, and it is the most common cause of death among those between 40 and 45 years of age. This disease will develop in about six to seven percent of women in the United States, and at the present time about one half of this group can be cured. The treatment of breast cancer involves surgery, radiation, chemotherapeutics and hormonal therapy, the last category including consideration of antiestrogens for treatment of endocrine-responsive tumors.

Tumors sensitive to estrogen stimulation may regress following competitive inhibition of estrogen receptors by tamoxifen (an antiestrogen). Response to tamoxifen is currently predicted based on the stage of disease and on the basis of assays for estrogen receptors (ER) and progesterone receptors (PR) in the tissue. Many breast cancers and all normal estrogen-responsive tissues contain these labile cytoplasmic proteins which bind estrogen and progesterone. Patients with positive assays for these proteins have an objective response to hormone therapy of about 65%, while those with negative assays have an objective response rate of <10%. For postmenopausal women having a first recurrence of breast cancer with an ER+ or PR+ assay, tamoxifen therapy is the treatment of choice.

Notwithstanding strong interest in the use of antiestrogens in breast cancer treatment, however, incomplete knowledge of their basic pharmacology persists. Substituted triphenylethylenes (including tamoxifen) have antiestrogen effects which appear to be partially dependent on geometric isomerism. For example, trans-tamoxifen (the isomer used in tamoxifen therapy) is an antiestrogen, whereas the cis isomer is a weak estrogen. The present invention makes use of newly acquired knowledge about in vivo interconversion of tamoxifen geometric isomers as well as the formation of tamoxifen metabolites, including estrogenic metabolites, to improve treatment of breast cancer.

Although tamoxifen is the most widely used antiestrogen for treating breast cancer, development of tamoxifen resistance and subsequent tumor progression during tamoxifen therapy represents a major reason for treatment failures. The mechanism of tamoxifen resistance has been unknown, but an estrogenic metabolite of tamoxifen which would promote growth in ER+ tamoxifen-resistant tumors is identified.

Tamoxifen (TAM) is a non-steroidal triphenylethylene antiestrogen which is commonly used in the treatment of patients with breast cancer. Tamoxifen competitively antagonizes the binding of estradiol to estrogen receptors, which is thought to be the mechanism for inhibiting tumor growth. However, tamoxifen also possesses both estrogenic as well as antiestrogenic effect. In other tissues such as human endometrial tissue, and in some species, such as dogs, tamoxifen acts as an estrogen agonist (Furr, 1984, Ferrazzi, 1977). The mechanisms underlying the "intrinsic" estrogenic effects of tamoxifen remain poorly understood. Because the estrogenic agonist/antagonist properties of tamoxifen are highly species and tissue dependent, it has been suggested that altered metabolic pathways leading to the production of estrogenic metabolites may be involved in the "intrinsic" estrogenic effects noted with tamoxifen.

The systemic metabolism of tamoxifen is characterized in humans. Pharmaceutically administered trans-tamoxifen is metabolized in the liver to N-desmethyl- and 4-hydroxytamoxifen (Adam, 1979), for example. Both of these metabolites are active antiestrogenic agents. N-desmethyltamoxifen is the major metabolite found in human serum. It is further metabolized to metabolite Z (didesmethyltamoxifen) and to metabolite Y, (the side chain alcohol) (Kemp, 1983, Jordan, 1983). At least two estrogenic metabolites of tamoxifen have been identified, these include metabolite E (monophenol) and bisphenol (Lyman 1985). Neither metabolite has been identified in any significant quantity in human serum or tissues. However, the monophenol has been isolated from the bile of dogs, a species in which tamoxifen is predominantly estrogenic (Fromson 1973).

It has been shown that tamoxifen can actually stimulate tumors to grow following chronic dosing in hormone responsive human tumor-bearing mouse models. The present inventors have shown that reduced uptake and metabolism of tamoxifen is associated with tamoxifen resistance and tamoxifen stimulated growth. The possibility that tumor cell growth is dependent on the net estrogenic agonist/antagonist activity of cellular compounds, including tamoxifen metabolites at the receptor site, led the present inventors to further explore whether estrogenic metabolites are present in neoplastic breast tissues. The presence of monophenol tamoxifen (metabolite E) in human breast tumor biopsy specimens is described herein using mass-spectrometry and HPLC identification techniques.

SUMMARY OF THE INVENTION

The present invention relates to the levels of tamoxifen isomers and metabolites as early indicators of tamoxifen resistance (prior to clinical treatment failure). Tamoxifen is representative of a group of compounds called triphenylethylene antiestrogens, whose effect is to slow or stop the growth of estrogen-dependent tumors. While it is the most commonly used drug for treatment of breast cancer today, tamoxifen is associated with the development of drug resistance in virtually all patients who take it. With the onset of resistance, tumor growth resumes or accelerates and tamoxifen therapy should be discontinued. Renewed tumor growth will eventually become obvious, of course, but an objective of the present invention is to provide early warning of tamoxifen resistance so that therapy can be changed promptly as needed.

The mechanism of tamoxifen resistance is incompletely described, but it is known that tamoxifen exists as two geometric isomers, the trans form (an antiestrogen) and the cis form (a weak estrogen). The trans form, of course, is the therapeutic drug for breast cancer. Further, however, it has been shown that there can be interconversion from one isomer to the other, especially with the 4-OH metabolite, in tissue culture cells and also, presumably, in patients.

A model with which the present invention was developed consists of human breast cancer cells growing subcutaneously in athymic nude mice. Treatment of the mice with tamoxifen results in tumor growth inhibition for four to six months, followed by the onset of tumor resistance and regrowth (much as in humans). Further, tumor regrowth is actually stimulated by tamoxifen. Even when such a tumor is transplanted into different mice, the resistant tumors will not grow unless stimulated by tamoxifen or estrogen. Tamoxifen, in these cases, appears to mimic the action of estrogen.

The development of tamoxifen resistance relates to conversion over time of both tamoxifen and its metabolites from trans (antiestrogen) forms to cis forms or conversion of tamoxifen to other metabolites which have estrogen-like activity. Assays for both trans and cis forms of tamoxifen as well as tamoxifen metabolites may be accomplished, for example, with a high performance liquid chromatography (HPLC) system and mass spectrographic analysis, in some cases. In results described herein, it is shown that:

1) tumors from tamoxifen-resistant mice have significantly lower concentrations of tamoxifen than sensitive tumors (whose growth is still arrested);
2) there is an increase in the cis-4-hydroxytamoxifen/trans-4-hydroxytamoxifen (C/T-OH-TAM) ratio in resistant tumors; and
3) there is a spectacular decrease in the ratio of tamoxifen to tamoxifen monophenol metabolite in resistant tumors.

Values of the C/T-OH-TAM ratio are about 0.4–0.5 in sensitive tumors and 0.8–0.9 in resistant tumors. The increased estrogen effect resulting from an elevated C/T-OH-TAM ratio may be the reason for development of resistance, the association appears to be consistent. Analogous and even more clear correlations are shown between the development of tamoxifen resistance and the appearance of certain tamoxifen metabolites such as tamoxifen metabolite E (monophenol). The ratio (ng/gm tissue) of total tamoxifen to metabolite E (tamoxifen monophenol), for example, decreases spectacularly as tamoxifen resistance develops.

BRIEF DESCRIPTION OF THE DRAWINGS

FIG. 13 shows HPLC chromatograms showing tamoxifen and metabolites in (FIG. 13A) MCF-7 tamoxifen resistant tumor grown in a nude mouse following tamoxifen administration (500 ug/d×6 mos) and (FIG. 13B) in a plasma sample spiked with bisphenol (a), monophenol (b), cis 4-hydroxytamoxifen (c), trans-4-hydroxytamoxifen (d), tamoxifen (e) and N-desmethyltamoxifen (f).

DETAILED DESCRIPTION OF PREFERRED EMBODIMENTS

Figure 1A:
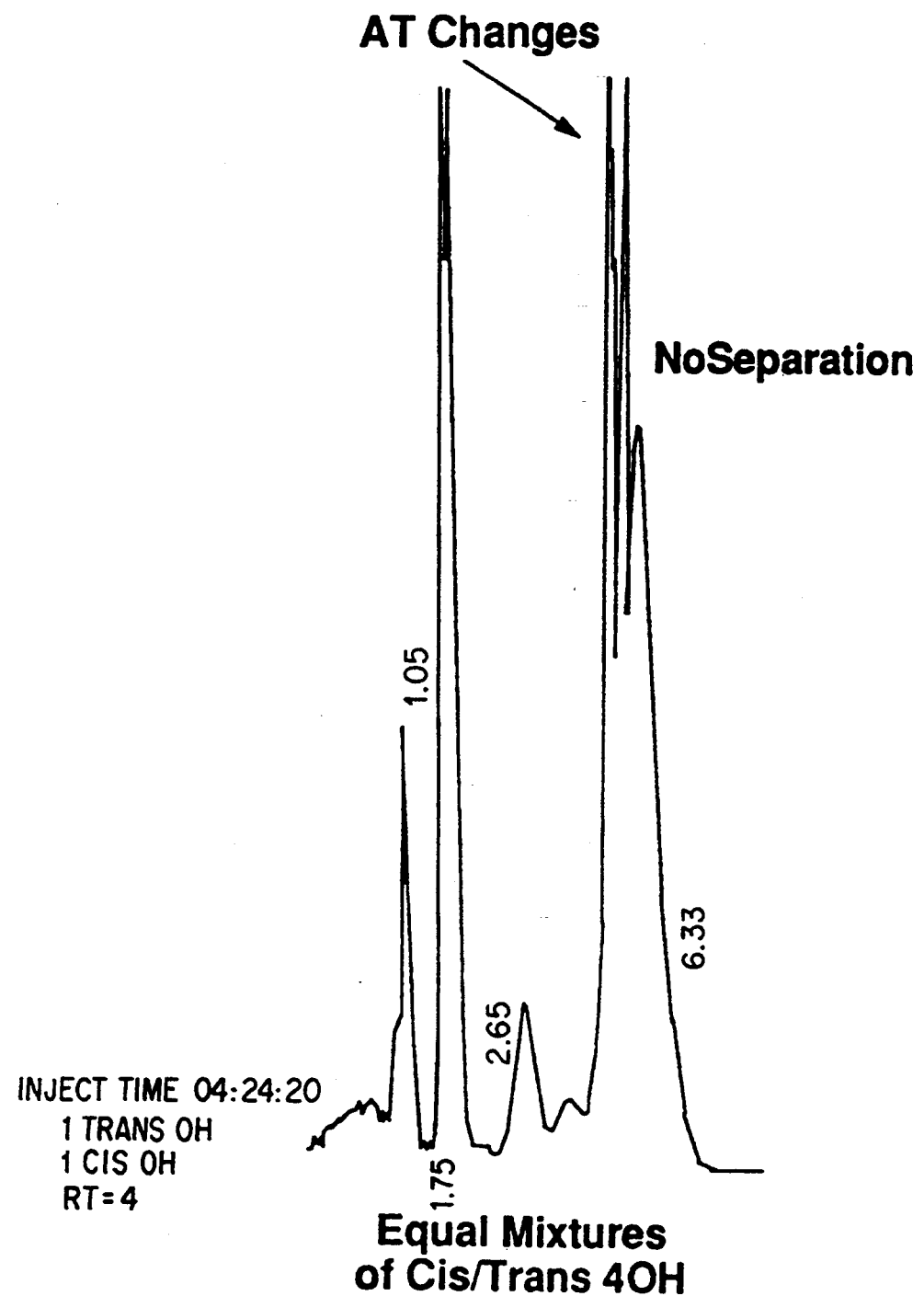
FIG. 1 shows HPLC tracings of 400 ng/ml stock solutions of trans and cis 4-hydroxytamoxifen (4-OH-TAM), respectively.

Those skilled in the art will recognize that changes analogous to those detected in the C/T-OH-TAM ratio or TAM/monophenol ratio may occur for other tamoxifen metabolites (e.g. particularly estrogenic metabolites such as bisphenol) or in other triphenylethylene antiestrogens related to tamoxifen. Nevertheless, the best mode of implementing the present invention now appears to be in conjunction with treatment of estrogen-responsive breast cancer with tamoxifen and detection of the onset of tamoxifen resistance.

Those skilled in the art will also recognize that if geometric isomerization or metabolism to other estrogenic metabolites proves to be the mechanism of antiestrogen resistance, synthesis of antiestrogens which preclude isomerization or metabolization will be a fruitful path to improved treatment. At the present time, however, tamoxifen is the drug of choice for hormonal treatment of recurrent breast cancer, and its invariable association with the onset of tumor resistance and tamoxifen-enhanced tumor growth makes the present invention a valuable aid to therapy.

Claims of the present invention are directed to indicators discovered to be closely associated with the onset of tumor tamoxifen resistance. Elevation of the C/T ratio for 4-OH-TAM, reduction in the TAM/monophenol ratio in tumor blood or other body fluid, and depression of the tamoxifen concentration in tumor are, for example, shown to be useful predictors of recrudescence of tumor growth despite (and perhaps in-part because of) tamoxifen treatment. The elevation of tamoxifen metabolite E(monophenol) concentrations, particularly with respect to tamoxifen concentrations is a preferred useful predictor. Other relevant ratios for such determinations include levels of estrogenic tamoxifen metabolites as compared to tamoxifen or any antiestrogenic tamoxifen metabolite. These indicators can be used individually or together.

For each indicator, small changes (for example, about a few percent) in the direction indicated by this specification and claims show early stages of tumor resistance. Larger indicator changes (up to about 80 to 100 percent, for example) are expected when tumor resistance is well established. Examples of in vitro and in vivo tests are provided to demonstrate the specific utility of the claimed invention and to support both the approximate magnitude of indicator changes and the reasonable extrapolations suggested in this specification. Those of skill in the art recognize that there are many methods of assay for tamoxifen, tamoxifen isomers and tamoxifen metabolites, particularly estrogenic ones. The development of antibodies, especially monoclonal antibodies, having specificities for tamoxifen and tamoxifen-related compounds will lead to ready assay methods of perhaps even greater clinical usefulness.

Examples presented herein show that acquired tamoxifen resistance is associated with reduced tamoxifen concentrations and increasing cis- to trans-4-hydroxytamoxifen ratios. The identification of monophenol tamoxifen metabolite in a tamoxifen resistant human breast tumor represents the first evidence that an estrogenic metabolite is also present in these tissues following prolonged tamoxifen treatment. Reduced accumulation of antiestrogenic compounds coupled with production of estrogenic metabolites may result in a net estrogenic environment within hormonally sensitive breast cancer cells. This observation explains why at least some tamoxifen resistant tumors are stimulated to grow by tamoxifen in various animal models. Further evidence of tamoxifen stimulated growth is seen in patients who are progressing on tamoxifen and respond to the discontinuation of tamoxifen with no other therapy. This also suggests that tamoxifen is directly or indirectly behaving like an estrogen agonist.

Those skilled in the art know that tamoxifen metabolites and isomers may be detected in tumor tissue or other fluids such as blood leukocytes, blood serum or blood plasma, for example.

These examples are presented to describe preferred embodiments and utilities of the present invention and are not meant to limit the present invention unless otherwise specified in the claims appended hereto. Taken together, the examples illustrate the best mode of implementing the invention as it is currently understood.

EXAMPLE 1

Mouse MCF-7 Tumor Model

In order to examine the relationship between tamoxifen metabolites and tamoxifen resistance, athymic Balb/c nude mice were implanted with human breast cancer tumor cells (MCF-7). Mice were treated daily for 4-6 months with subcutaneous tamoxifen. After tamoxifen resistance developed and tumor progression was observed, mice were sacrificed, and tumors were collected. In addition, tamoxifen-sensitive tumors were collected from mice still responding to tamoxifen therapy.

Analytical Methodology

Quantification of tamoxifen and its metabolites in tumor specimens was performed using photoactivation and high performance liquid chromatography (HPLC) analysis. To summarize: Each tumor sample was weighed, spiked with an internal standard, and homogenized. Tissue samples were then extracted with 2% n-butanol in hexane and irradiated with high intensity ultraviolet light (254 nm). Samples were analyzed by HPLC using a C-18 reverse phase column and eluted isocratically with a mobile phase of water (7%) and triethylamine (0.25%) in methanol. All solvents were of HPLC grade. Fluorescence of all compounds was measured at a wavelength of 266 nm. The sensitivity of this assay was approximately 2 ngs/gm for trans-tamoxifen, n-desmethyltamoxifen and cis and trans-4-hydroxytamoxifen. Linearity was measured through a concentration range of 25–3,000 ngs for all compounds, with a correlation coefficient of greater than 0.993. Cis and trans-4-hydroxytamoxifen ratios were calculated based on peak-heights. In some samples, the tumor was first homogenized and then the nuclear pellet obtained by centrifugation. HPLC tamoxifen measurements were made on extracts of the entire tumor specimen or on subcellular fractions including the cytosol or-the total nuclear pellet. In some cases, the nuclear pellet was further extracted in 0.4M KCl to extract primary metabolites bound to estrogen receptor.

Chromatographs (Mouse Studies)

Figure 1C:
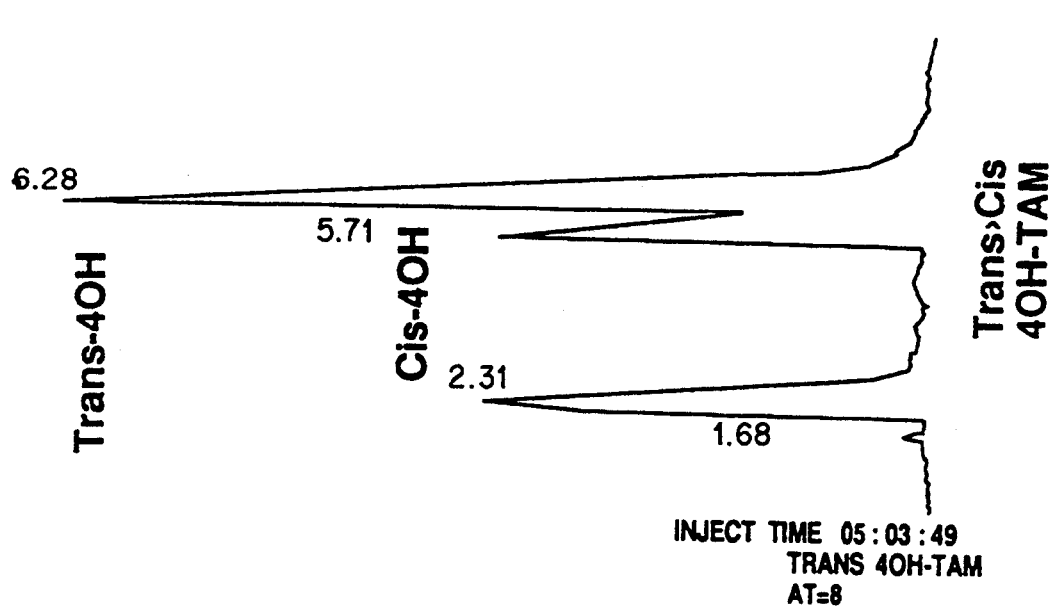
Figure 1B:
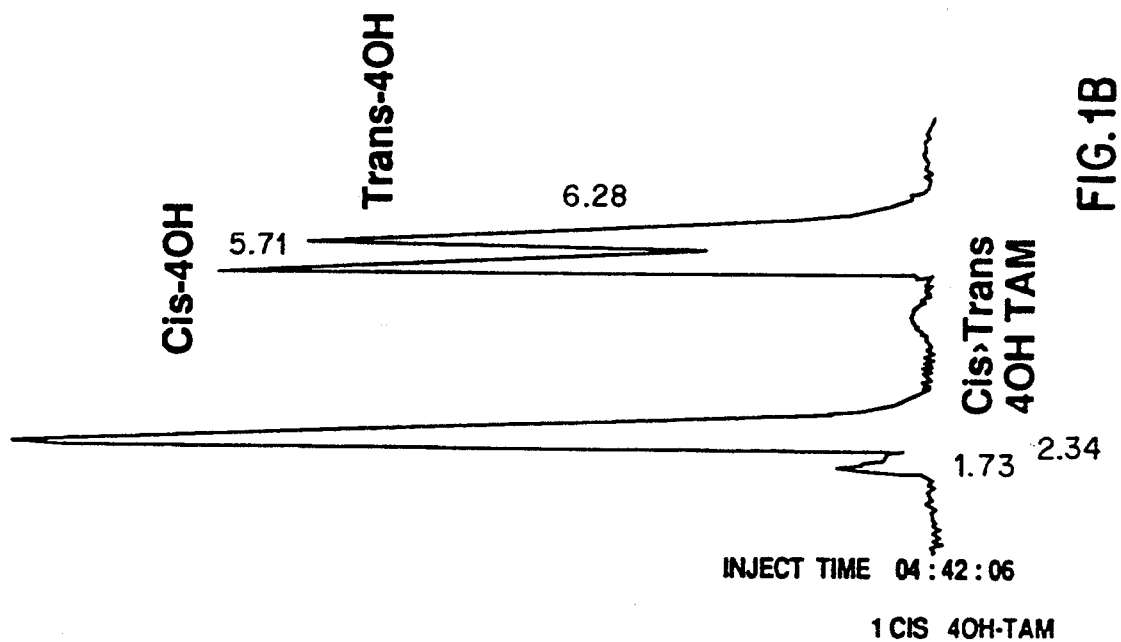

HPLC tracings (see FIG. 1) are shown of 400 ng/ml stock solutions of trans and cis 4-OH-TAM isomers mixed so as to yield a solution with equal amounts, as well as a solution in which the trans isomer predominated and one in which the cis isomer predominated. These tracings show that specimens may be analyzed to determine relative amounts of the geometric isomers present, thus providing a means of easily following a patient's response to tamoxifen therapy using a method of the present invention.

Figure 2A:
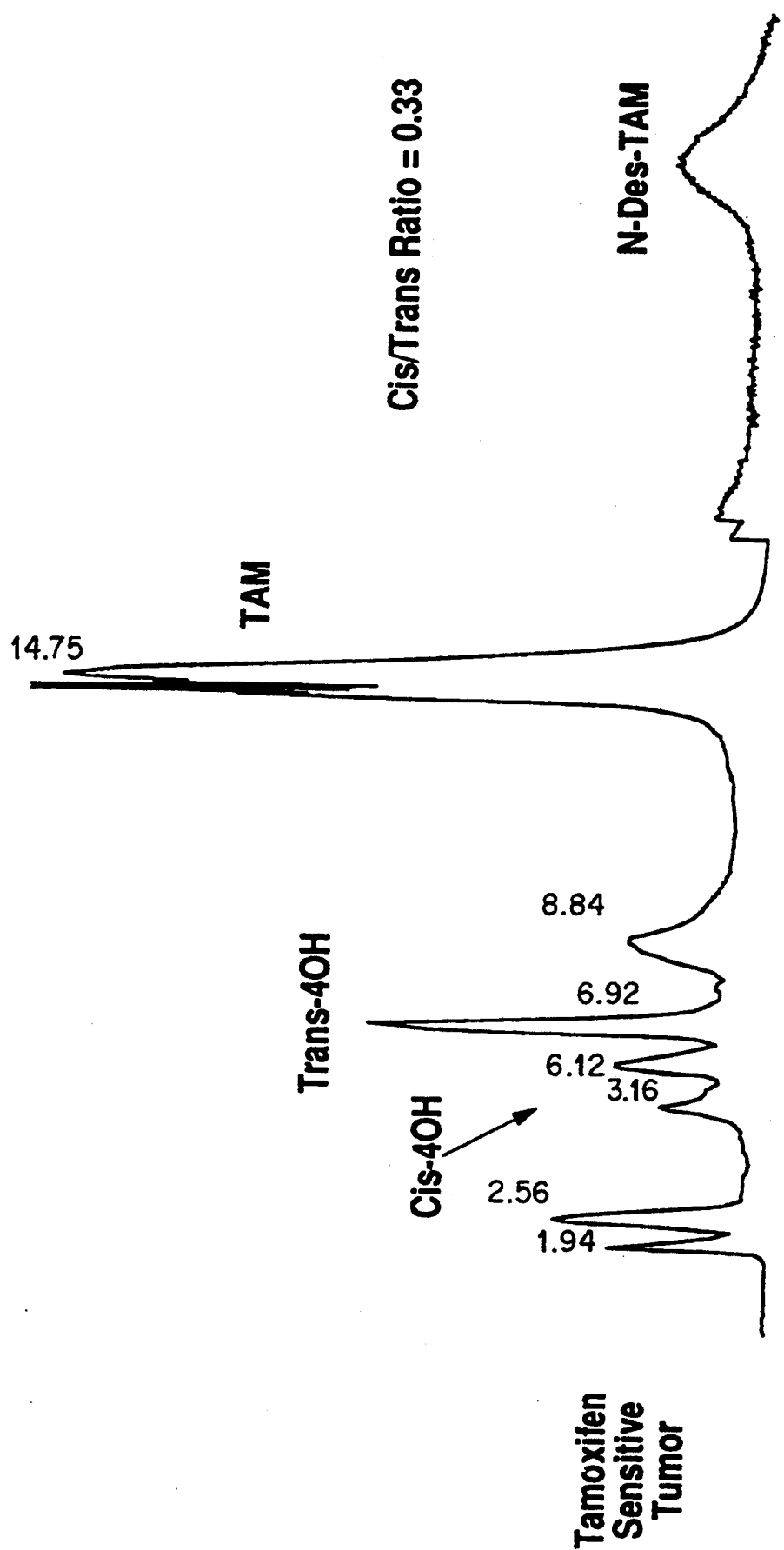
FIG. 2 shows HPLC chromatographs indicating that the cis/trans ratio of 4-OH-TAM is lower in sensitive than in resistant tumors isolated from athymic nude mice.
Figure 2B:
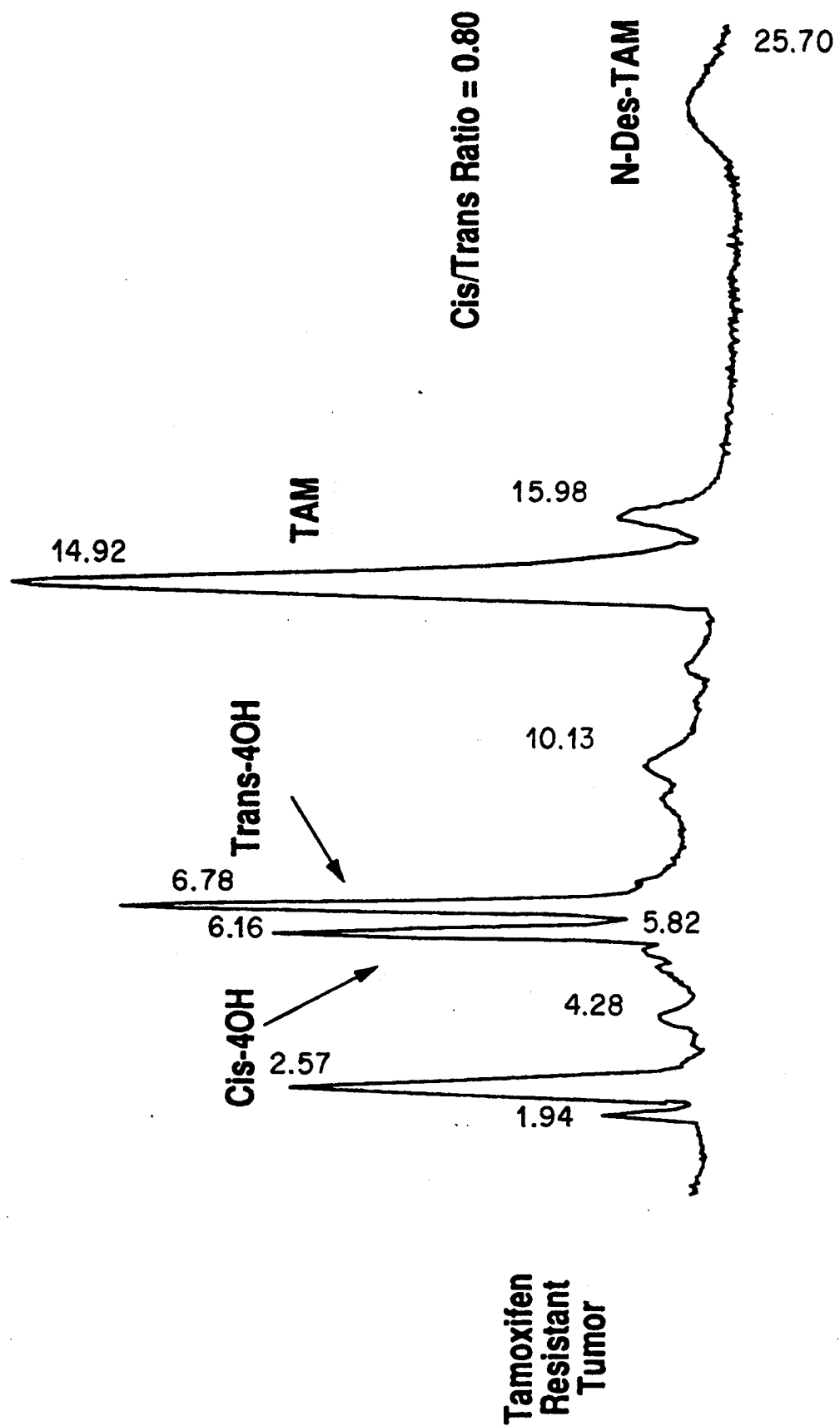

FIG. 2 shows HPLC tracings indicating relative amounts of trans and cis 4-OH-TAM in sensitive and resistant tumors isolated from tamoxifen-treated athymic nude mice. These figures demonstrate identification of cis and trans 4-OH-TAM in tamoxifen-resistant and sensitive tumors. Further, they demonstrate that the cis/trans ratio is higher in the resistant tumor.

Figure 3:
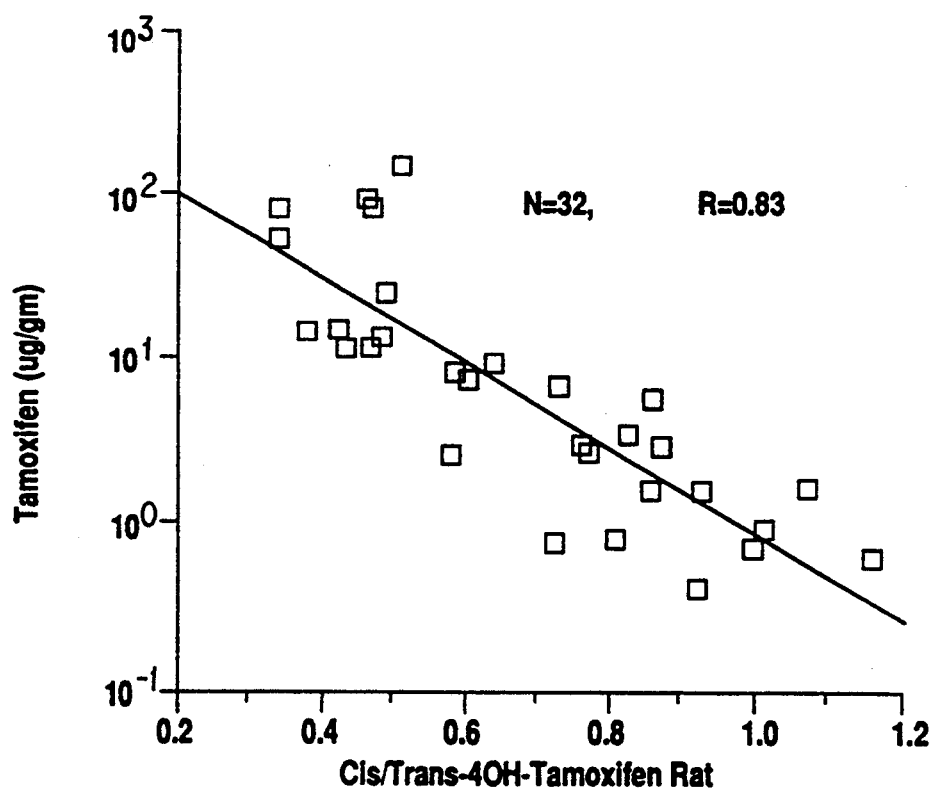
FIG. 3 shows the approximately linear inverse relationship which exists between the logarithm of total tumor tamoxifen concentration and the cis/trans 4-OH-TAM ratio (N=32, R=0.83, linear regression analysis)

FIG. 3 shows the approximately linear inverse relationship of the logarithm of total tumor tamoxifen concentration to cis/trans 4-OH-TAM ratios (N=32, R=0.83, linear regression analysis). This graph suggests that because total tumor tamoxifen concentration is related to the geometric isomer ratio, only one of these quantities may be needed to predict emergence of tumor resistance. Because determination of the isomer ratio does not require absolute concentrations, it may be a more convenient measure for clinical evaluation of tamoxifen-treated patients.

Figure 4:
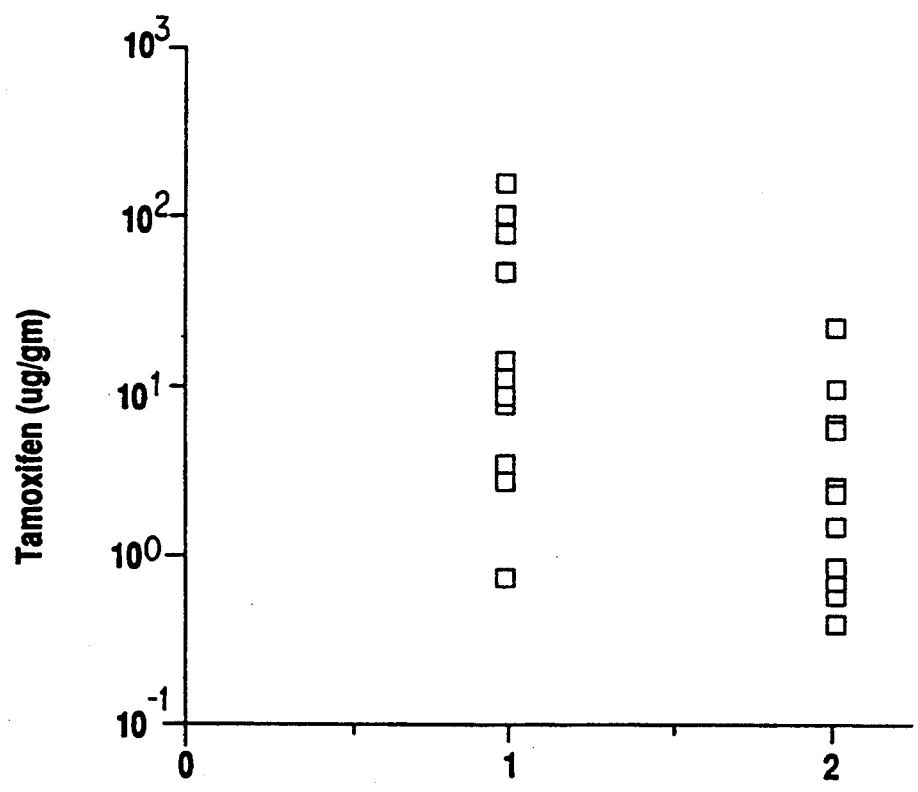
FIG. 4 shows a scatter plot of tamoxifen concentrations in sensitive and resistant MCF-7 tumors (N=32).

FIG. 4 shows a scatter plot of tamoxifen concentrations in sensitive and resistant MCF-7 tumors (N=32). Mean tamoxifen concentrations in sensitive tumors is 36 ug/gm (SD=46.41), versus 4.38 ug/gm in resistant MCF-7 tumors (SD=6.22). These differences are highly statistically significant (P<0.0005) by the Wilcoxon Rank Sum test. See Table 1 for Data.

The median tamoxifen concentration in sensitive tumors is 12.475 ug/gm and in resistant tumors it is 2.2 ug/gm. 10 of 16 sensitive tumors had values greater than 10 ug/gm compared to only 2 of 16 resistant tumors. This graph implies that while individual tamoxifen concentrations might not be determinative of tamoxifen resistance, a trend in such numbers for a particular patient could be helpful in making therapeutic decisions.

TABLE 1

Tamoxifen Concentrations in Sensitive and Resistant MCF-7 tumors.

| (N = 16) | Tamoxifen (ug/gm) | |
|---|---|---|
| | Sensitive (N = 16) | Resistant |
| 1. | 101.55 | 1.82 |
| 2. | 84.47 | 25.12 |
| 3. | 10.76 | 6.93 |
| 4. | 159.24 | 3.3 |
| 5. | 80.94 | 2.58 |
| 6. | 12.69 | 6.08 |
| 7. | 50.7 | 0.745 |
| 8. | 15.36 | 0.688 |
| 9. | 0.766 | 3.348 |
| 10. | 2.78 | 0.45 |
| 11. | 8.85 | 1.64 |
| 12. | 8.08 | 0.814 |
| 13. | 12.26 | 11.12 |
| 14. | 9.45 | 1.66 |
| 15. | 14.4 | 2.81 |
| 16. | 3.79 | 0.981 |
| Mean | 36 ug/gm | 4.38 ug/gm | p < 0.0005

| SD = 46.41 ug/gm | SD = 6.22 ug/gm |
|---|---|
| Range = 0.77–159.24 | Range = 0.45–25.12 |
| 10/16 are > 10 ug/gm | 2/16 > 10 ug/gm |
| median = 12.475 ug/gm | median = 2.2 ug/gm |

Figure 5:
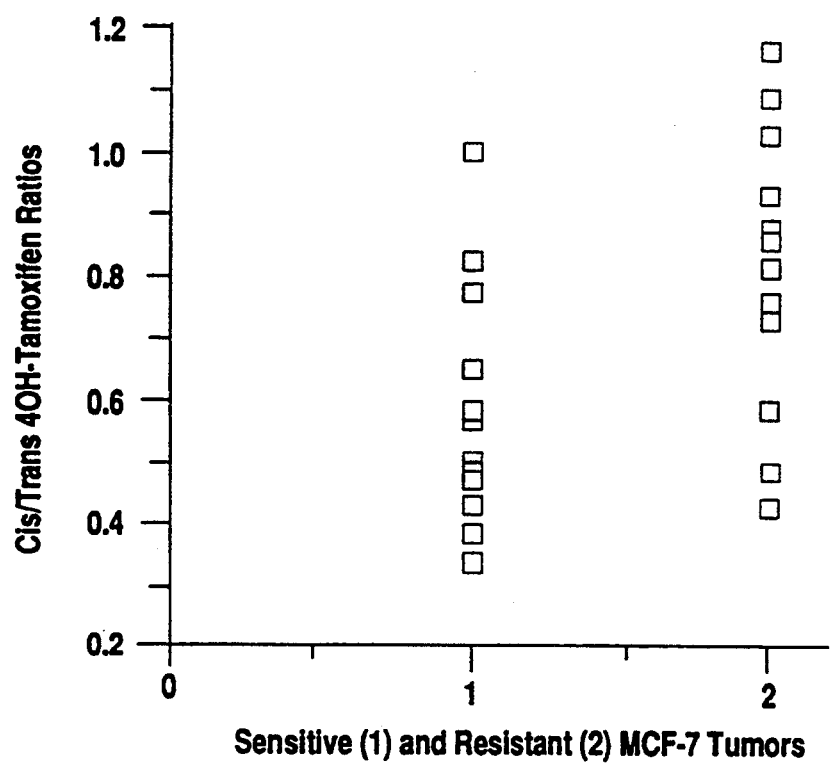
FIG. 5 shows a scatter plot of 4-OH-TAM ratios (cis/trans) in sensitive and resistant MCF-7 tumors (N=32).

FIG. 5 shows a scatter plot of cis/trans 4-OH-TAM ratios in sensitive and resistant MCF-7 tumors (N=32). The mean 4-OH-TAM cis/trans ratio in sensitive tumors was 0.5297 (SD=0.168), whereas in resistant MCF-7 tumors the mean ratio was 0.8141 (SD=0.196). These differences are again highly statistically significant (P<0.0005). See Table 2 for cis/trans 4-OH-TAM data.

By reasoning similar to that for FIG. 4, this graph indicates that while individual cis/trans ratio determinations might not be determinative of tamoxifen resistance, a trend in such numbers for a particular patient would be helpful in making therapeutic decisions.

TABLE 2

Cis/trans 4-OH-TAM ratios in sensitive and resistant MCF-7 tumors.

| | Cis/Trans 4OH-Tamoxifen | |
|---|---|---|
| | Sensitive (N = 16) | Resistant (N = 16) |
| 1. | 0.575 | 0.86 |
| 2. | 0.588 | 0.812 |
| 3. | 0.472 | 0.442 |
| 4. | 0.56 | 0.929 |
| 5. | 0.645 | 1.019 |
| 6. | 0.428 | 0.777 |
| 7. | 0.446 | 1.073 |
| 8. | 0.4632 | 0.49 |
| 9. | 0.476 | 0.724 |
| 10. | 0.506 | 0.868 |
| 11. | 0.34 | 0.59 |
| 12. | 0.486 | 0.86 |
| 13. | 0.34 | 0.73 |
| 14. | 0.38 | 1.16 |
| 15. | 1.0 | 0.76 |
| 16. | 0.77 | 0.932 |
| Mean | 0.5297 | 0.8141 | p < 0.0005

| SD = 0.168 | SD = 0.196 |
|---|---|
| Range = (0.34–1.0) | Range = (0.442–1.16) |
| Median = 0.48 | Median = 0.84 |
| 3/16 > 0.06 | 3/16 ≦ 0.60 |
| 13/16 ≦ 0.60 | 13/16 > 0.60 |

Figure 6:
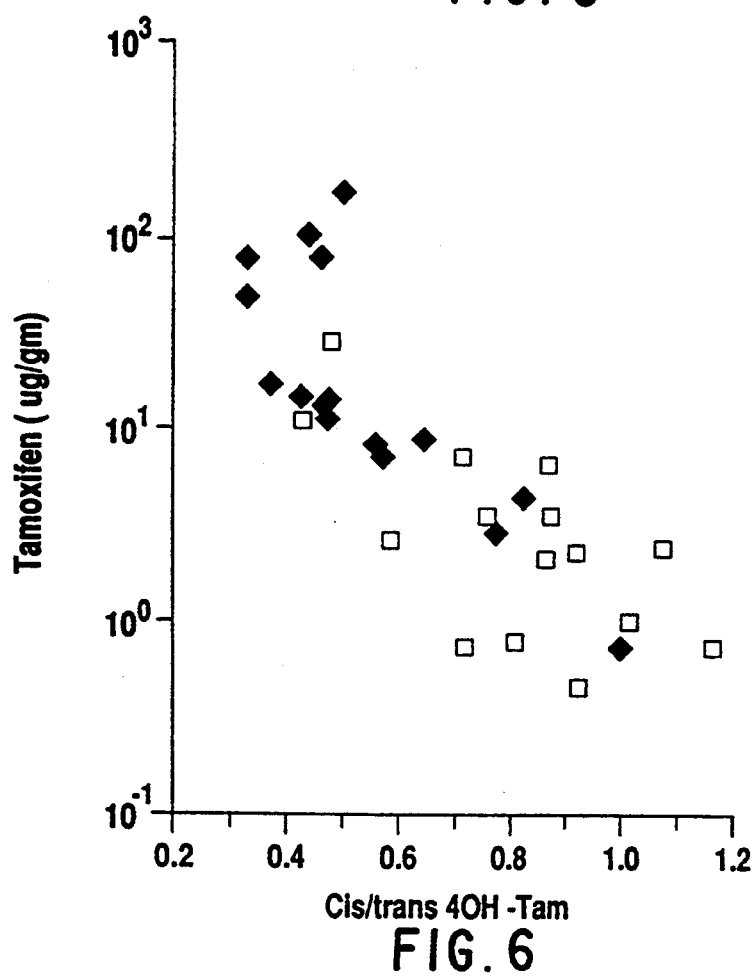
FIG. 6 shows a scatter plot of tamoxifen versus cis/trans 4-OH-TAM ratios in resistant tumors (open symbols) and sensitive tumors (solid symbols).

FIG. 6 shows the scatter plot of FIG. 3 except for removal of the regression line and addition of identification for resistant (open symbols) and sensitive (solid symbols) tumors. This scatter plot demonstrates the relationship among cis/trans ratios, total tumor tamoxifen concentration, and tamoxifen resistance. Resistant tumors have lower tamoxifen concentrations and higher cis/trans ratios. Nevertheless, this graph like FIGS. 3, 4, and 5 further indicates that trend data are even more useful in therapeutic decisions for a given patient than single determinations of either tamoxifen concentration or the cis/trans ratio.

Table 3 shows cis/trans ratios and tamoxifen concentrations in nuclear extractions versus nuclear pellets extracted with 0.4 molar KCl followed by 200,000 G centrifugation at 4°. The material extracted with KCl includes that bound to estrogen receptor. The results of this experiment suggest that tamoxifen-sensitive tumors generally have a higher percentage of the major antiestrogen metabolite, trans 4-OH-TAM. In addition, tamoxifen resistant tumors generally have reduced tamoxifen concentrations, together with high levels of the less antiestrogenic and more estrogenic metabolite cis 4-OH-TAM. Therefore, levels of geometric isomers of the 4-OH-TAM metabolite, together with tamoxifen levels, may indicate tumor sensitivity.

TABLE 3

Study #4 Tumors 2 to 13
Cis/Trans Ratios - Tamoxifen Levels - R/S

| tumor # | cis/trans ratio | tamoxifen level (conc/ g) | S/R |
|---|---|---|---|
| 2 Total Nuclear | 0.6846 | 3,440.28 | sensitive |
| 2 KCl Nuclear Extract | trans only | 664.26 | |
| 3 Total Nuclear | 1.0455 | 2,568.63 | sensitive |
| 3 KCl Nuclear Extract | — | 825.35 | |
| 4 Total Nuclear | 0.4620 | — | resistant |
| 4 KCl Nuclear Extract | 0.9195 | 798.48 | |
| 5 Total Nuclear | 0.6632 | 4,282.17 | sensitive |
| 5 KCl Nuclear Extract | trans only | 412.68 | |
| 6 Total Nuclear | 1.0209 | 796.78 | resistant |
| 6 KCl Nuclear Extract | 1.9248 | 157.96 | |
| 7 Total Nuclear | 0.9401 | 713.43 | resistant |
| 7 KCl Nuclear Extract | 1.3808 | 148.67 | |

TABLE 3-continued

Study #4 Tumors 2 to 13
Cis/Trans Ratios - Tamoxifen Levels - R/S

| tumor # | cis/trans ratio | tamoxifen level (conc/ g) | S/R |
|---|---|---|---|
| 8 Total Nuclear | 1.0059 | 1,891.92 | sensitive |
| 8 KCl Nuclear Extract | — | 454.25 | |
| 9 Total Nuclear | 0.3808 | 14,238.85 | sensitive |
| 9 KCl Nuclear Extract | 0.9351 | 1,330.48 | |
| 10 Total Nuclear | 0.8530 | 1,139.24 | resistant |
| 10 KCl Nuclear Extract | 2.2606 | 228.21 | |
| 11 Total Nuclear | 0.4924 | 8,757.46 | sensitive |
| 11 KCl Nuclear Extract | trans only | 950.92 | |
| 12 Total Nuclear | 1.0904 | 817.98 | resistant |
| 12 KCl Nuclear Extract | 2.0029 | 193.33 | |
| 13 Total Nuclear | 0.4367 | 8,062.12 | sensitive |
| 13 KCl Nuclear Extract | trans only | 1,667.69 | |

KCl Nuclear Extract fraction equals nuclear pellet extracted with 0.4 molar KCl followed by 200,000 G's.

Four of seven sensitive tumors had trans only in the KCl nuclear extract, in two the levels were below the limit of detectability and in one the C/T ratio was 0.9. All 5 resistant tumors had high C/T ratios. Total and KCl extracted tamoxifen was lower in resistant than in sensitive tumors.

Figure 7A:
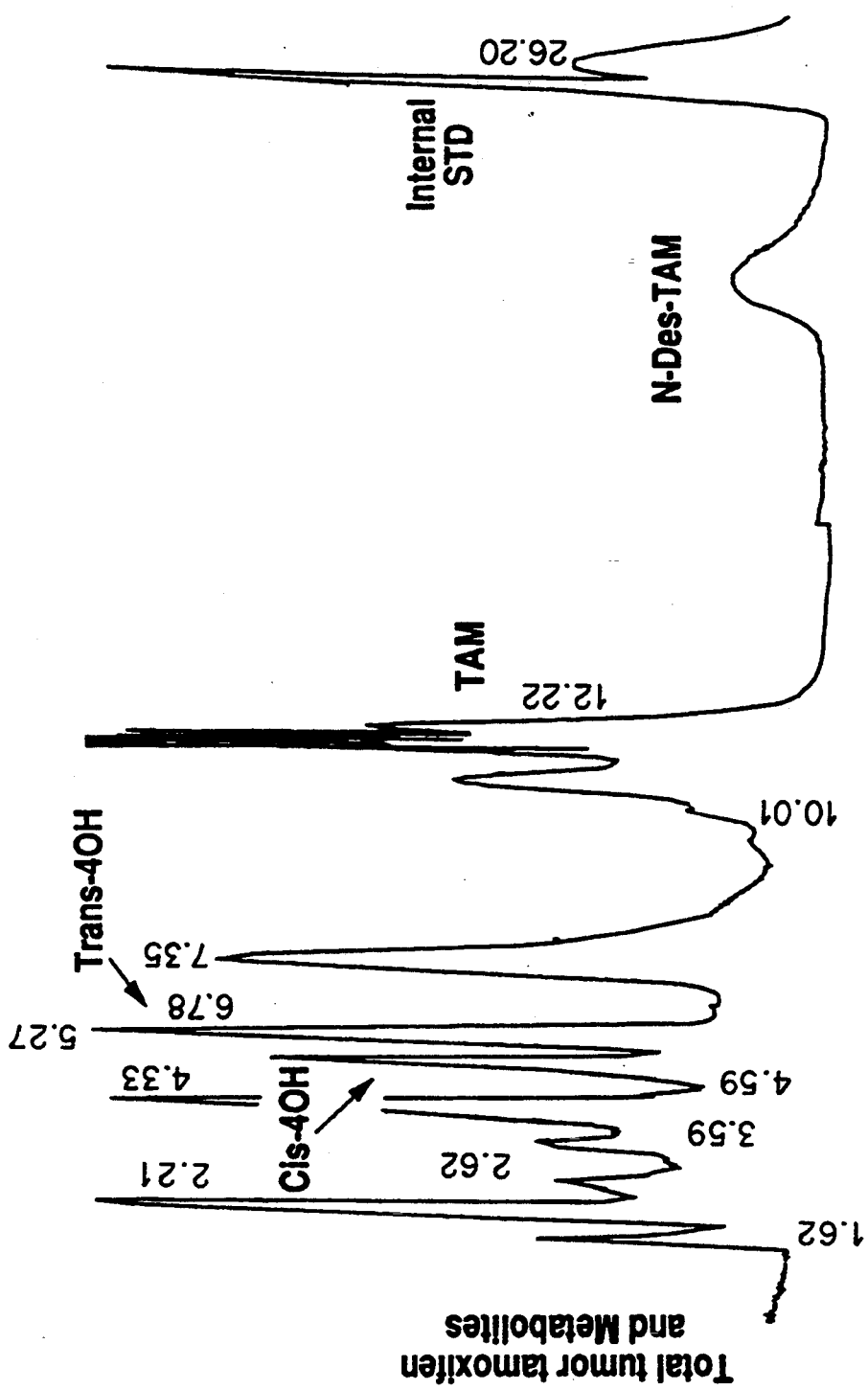
FIG. 7 shows HPLC chromatographs of a resistant tumor analyzed for total tumor tamoxifen, cytosol tamoxifen, and tamoxifen found in nuclear pellets extracted with KCl (from top to bottom, respectively).
Figure 7B:
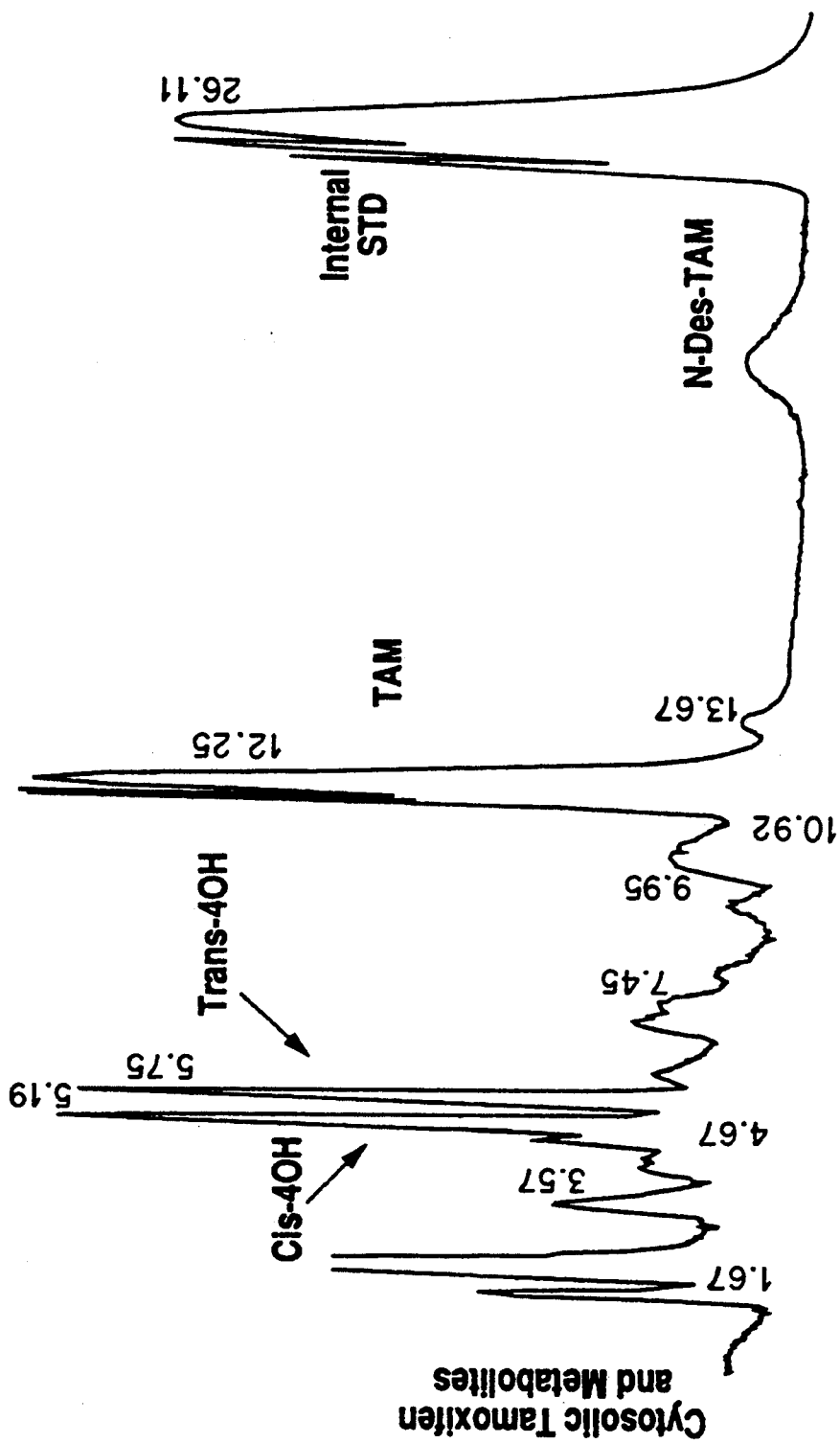
Figure 7C:
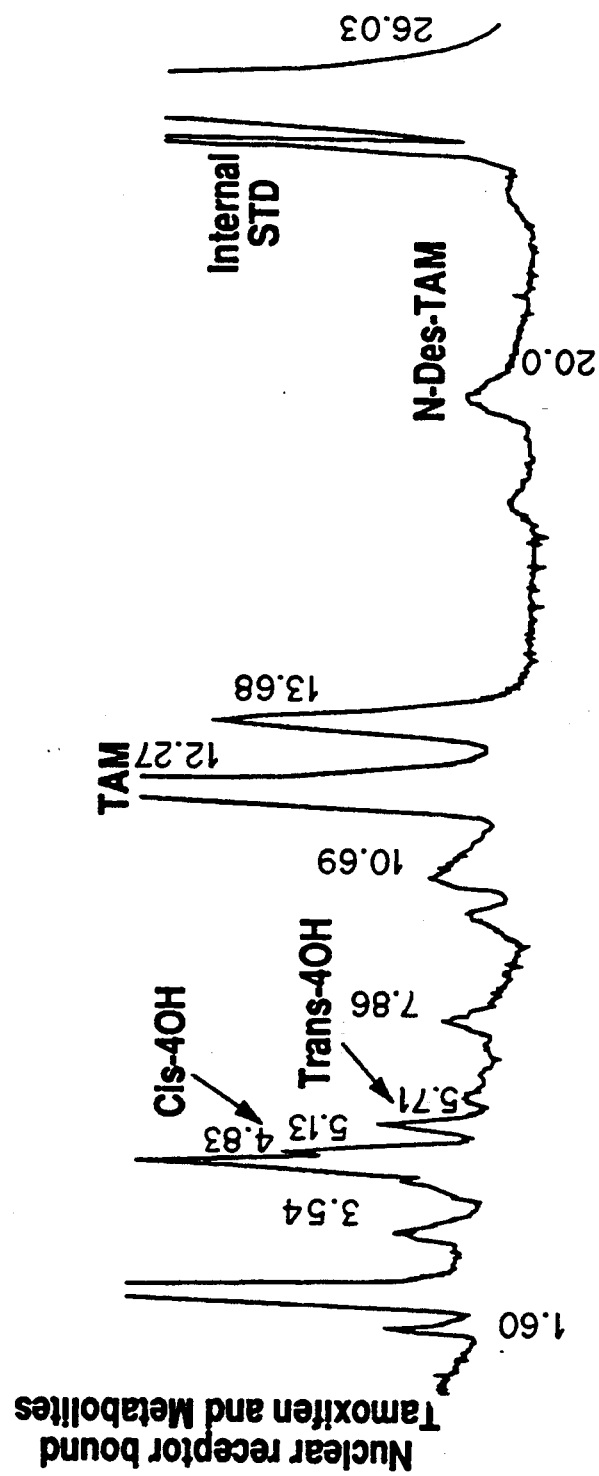

FIG. 7 shows an HPLC chromatograph of a resistant tumor analyzed for total tumor tamoxifen, cytosol tamoxifen, and tamoxifen found in nuclear pellets extracted with KCl (from top to bottom, respectively). This figure shows that cis 4-OH-TAM/trans-4-OH-TAM ratios are larger in the nuclear pellets extracted with KCl, which presumably represents estrogen receptor-bound drug. This observation indicates that tamoxifen resistance is related to the production of the cis 4-OH-TAM metabolite.

EXAMPLE 2

Human Studies

To further demonstrate that the invention is applicable in humans, several studies were carried out which demonstrate its feasibility. These include:

1) identification and measurement of tamoxifen and its metabolites in tumors isolated from tamoxifen-treated patients who are known treatment failures;
2) measurement of tamoxifen and its metabolites in serum from patients who are being treated with adjuvant doses of tamoxifen;
3) determination of cis/trans 4-OH-TAM ratios in treatment-resistant human tumors.

Table 4 shows tamoxifen concentrations and cis/trans ratios in 14 human tumor specimens from patients who were on tamoxifen therapy. There are two tamoxifen-sensitive tumors (L281 and G375) for comparison because patients responding to treatment are not usually biopsied during the responsive phase of their disease. The majority of patients whose tumors were tested had relatively high cis/trans ratios in the total tumor extract, as were noted with the MCF-7 mouse model. That is, tamoxifen-resistant human tumors have significant concentrations of the weakly antiestrogenic metabolite, cis 4-OH-TAM, a metabolite which may also have weak estrogenic activity. The two tumors from tamoxifen-sensitive patients, as expected, have low cis/trans ratios.

TABLE 4

Tamoxifen/Metabolites in Total Tumor, Cytosol, and Nuclear Pellets Extracted with 0.4 molar KCl

Figure 8A:
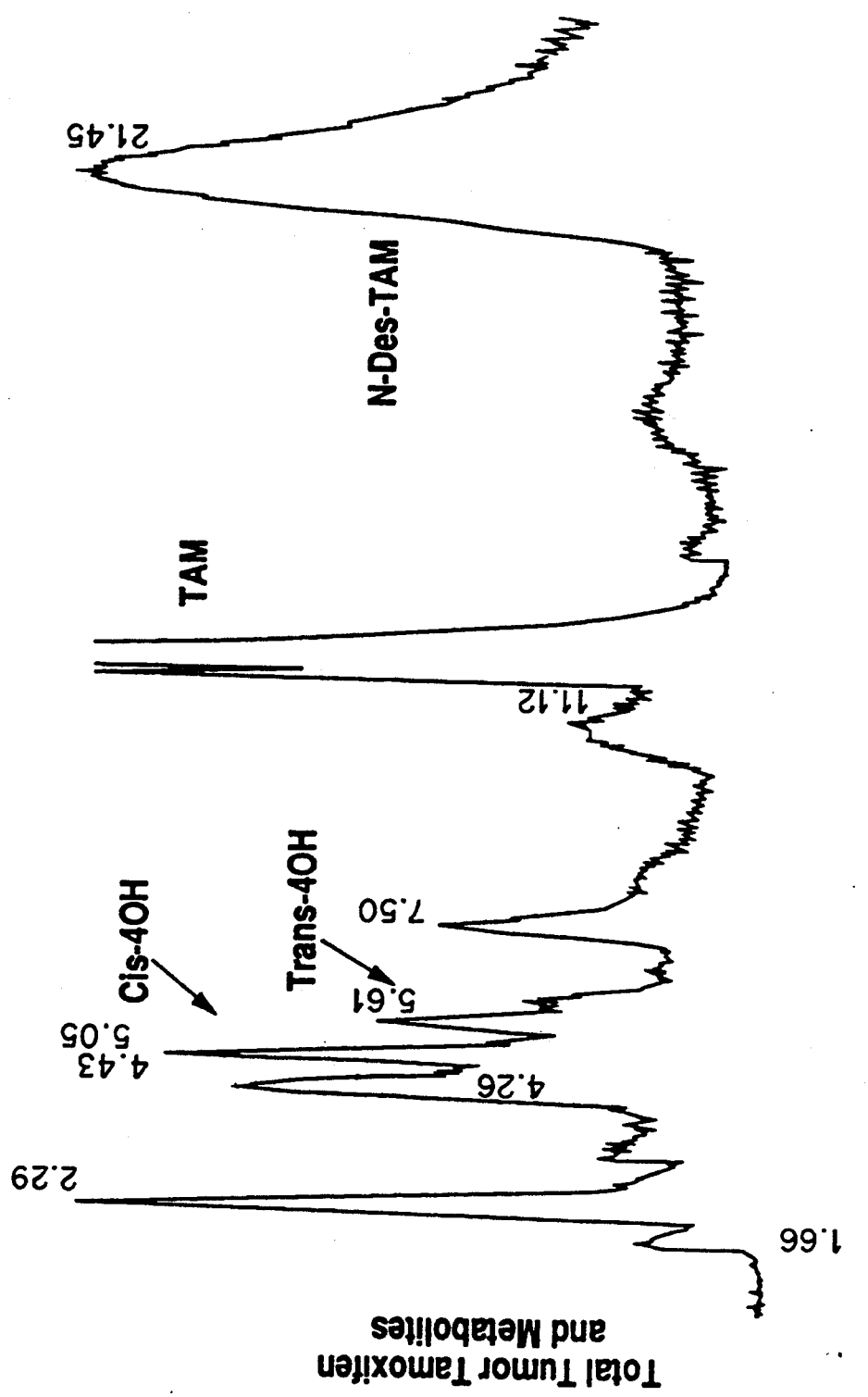
FIG. 8 shows example HPLC chromatographs demonstrating concentrations of cis- and trans-4-OH-TAM extracted from tumor nuclear pellets representing patients with clinically-evident tumor resistance. These findings of greater cis than trans levels must be contrasted with analogous measurements for tamoxifen-sensitive tumors in the mouse model (showing trans>cis 4-OH-TAM) because sensitive tumors in human patients are not biopsied and the information is not available.
Figure 8B:
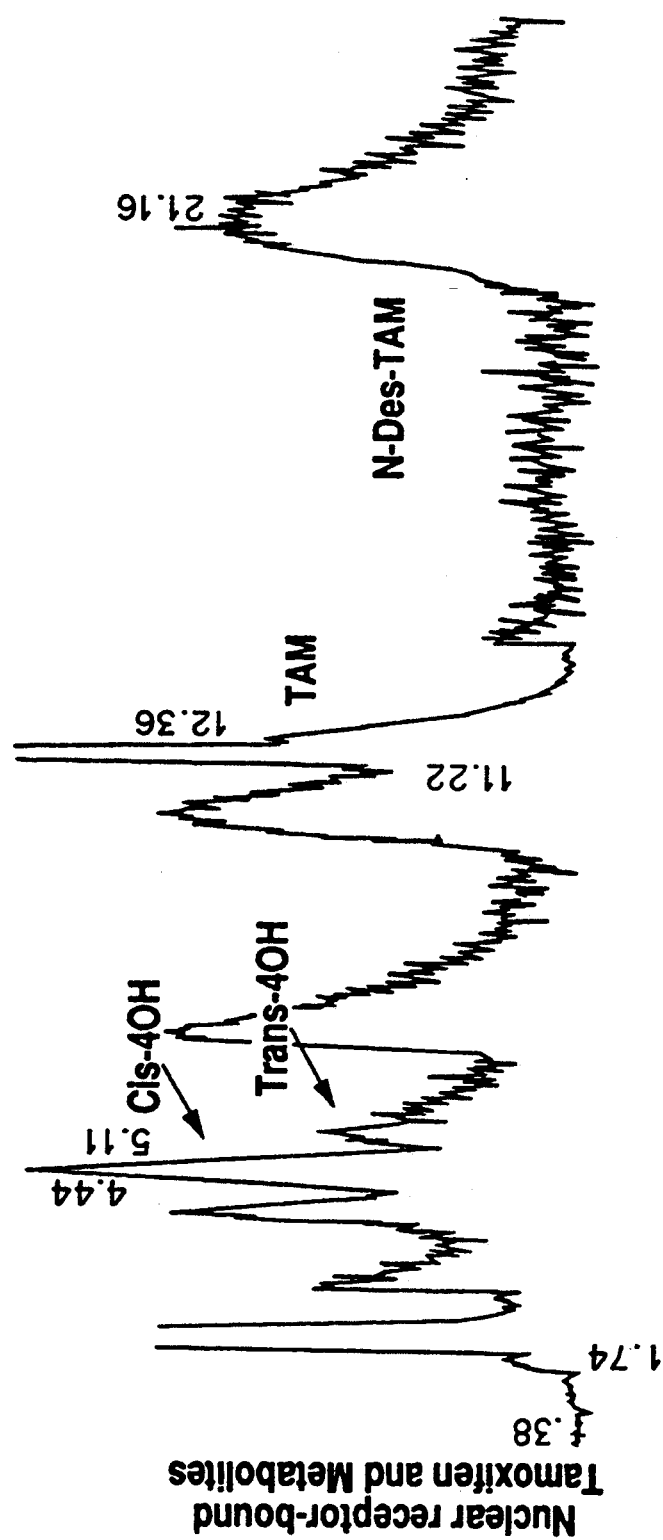
Figure 8C:
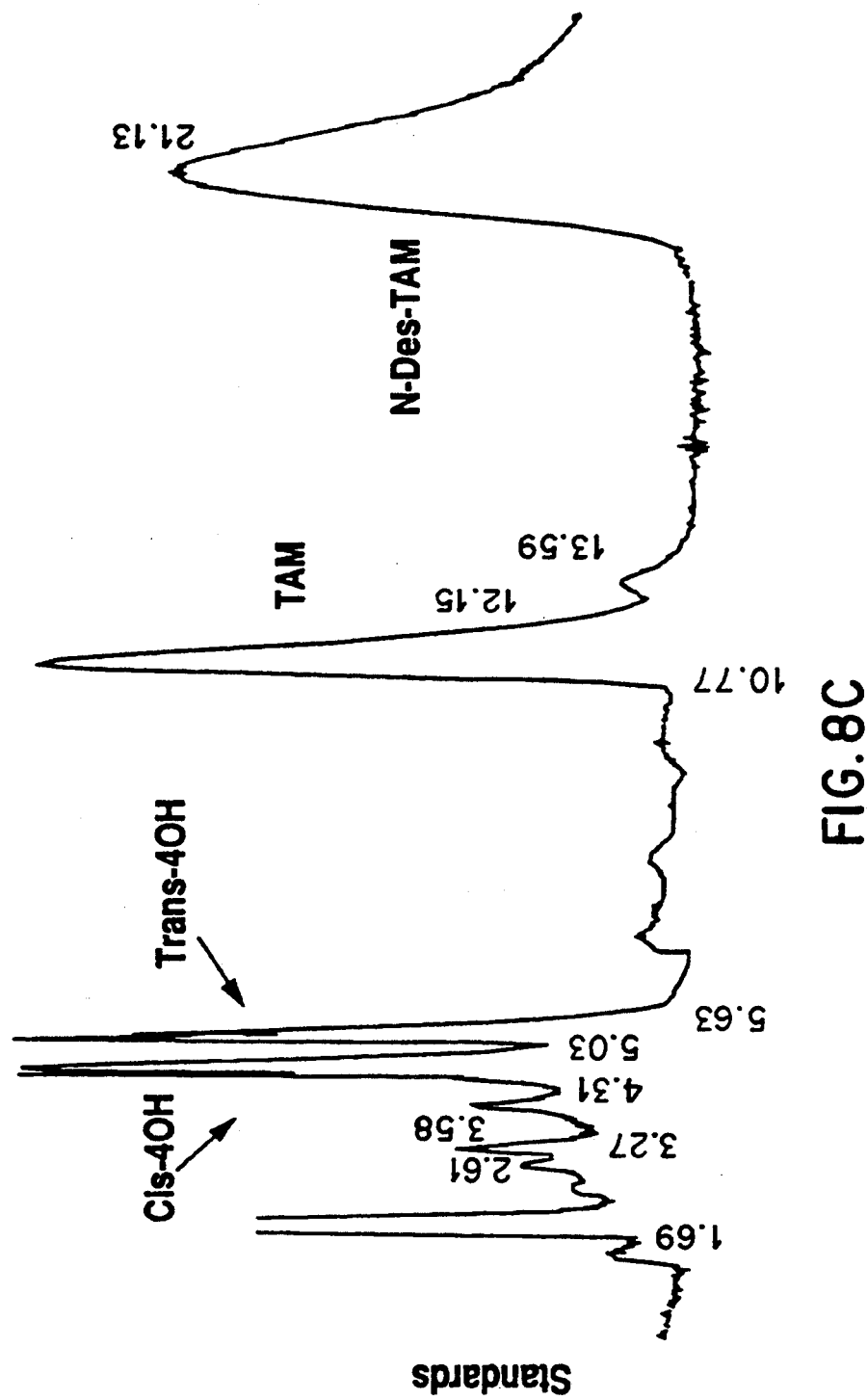

| sample patient # | | weight (mg) | Tamoxifen peak height | 4OH cis peak height | 4OH trans peak height | cis/trans ratio |
|---|---|---|---|---|---|---|
| W 131 | total | 41 | 57789 | 4587 | 3394 | 1.35 |
| | cytosol | 97 | 18504 | 1724 | 902 | 1.91 |
| | pellet | 97 | ni | 1496 | 1024 | 1.46 |
| N 184 | total | 38 | 1567 | ni | ni | 1.42 |
| | cytosol | 88 | 183 | 358 | nd | cis only |
| U 243 | total | 34 | 44604 | ni | ni | 1.23 |
| | cytosol | 77 | 9067 | 1544 | 1021 | 1.51 |
| | pellet | 77 | 5600 | ni | ni | 0.97 |
| L 281* | total | 44 | 39960 | 3324 | 12216 | 0.27 |
| | cytosol | 80 | 7369 | 1389 | 3787 | 0.37 |
| | pellet | 80 | 4795 | 1154 | 1194 | 0.97 |
| H 312 | total | 33 | 39726 | 3574 | 7749 | 0.46 |
| | cytosol | 87 | 15887 | ni | ni | 1.38 |
| | pellet | 87 | 3234 | ni | ni | 1.18 |
| G 375* | total | 49 | 17521 | 1911 | 3373 | 0.57 |
| | cytosol | 44 | 8429 | 613 | 723 | 0.85 |
| | pellet | 44 | 2523 | ni | ni | 1.29 |
| F 462 | total | 45 | 598 | ni | 3968 | trans only |
| | cytosol | 93 | 301 | 431 | 1102 | 0.39 |
| U 465 | total | 32 | 8823 | ni | 4287 | trans only |
| | total | 125 | 6672 | 640 | 1703 | 0.38 |
| | pellet | 125 | 2248 | 508 | nd | cis only |
| T 474 | total | 44 | 11987 | ni | 1481 | trans only |
| | total | 113 | 3129 | 483 | 741 | 0.65 |
| | pellet | 113 | 2737 | 311 | nd | cis only |
| Y 501 | total | 48 | 4085 | ni | ni | 1.19 |
| | cytosol | 71 | 1288 | 206 | nd | cis only |
| K 532 | total | 36 | 8850 | ni | nd | — |
| | total | 85 | 3410 | 669 | 324 | 2.06 |
| | pellet | 85 | 1131 | 305 | nd | cis only |
| I 559 | total | 65 | ni | ni | nd | — |
| | cytosol | 89 | 243 | 456 | nd | cis only |
| J 562 | total | 32 | 21965 | 3924 | nd | cis only |
| | cytosol | 64 | 6656 | 1291 | 784 | 1.48 |
| | pellet | 64 | 161 | ni | ni | 1.45 |
| J 578 | total | 36 | ni | ni | nd | — |
| | cytosol | 51 | 553 | 408 | nd | cis only | nd = not detectable
ni = no integration (ratio obtained by direct measurement)
total = total tumor
cytosol = total tumor except for the nucleus
pellet = KCl nuclear extract
*tamoxifen sensitive tumors Results of these studies show that concentrations of tamoxifen and its metabolites measured in serum, tumors, and nuclear fractions can be used to follow the response of human tumor patients. Relative increases in the cis/trans ratio and decreases in tamoxifen concentration, for example, are expected to be associated with patients whose tumors are progressing on adjuvant doses of tamoxifen. FIG. 8 shows an example of higher cis 4-OH-TAM in the nuclear pellets (extracted with 0.4 molar KCl, followed by ultracentrifugation, as in the mouse studies).

Human Serum Specimens

Figure 9A:
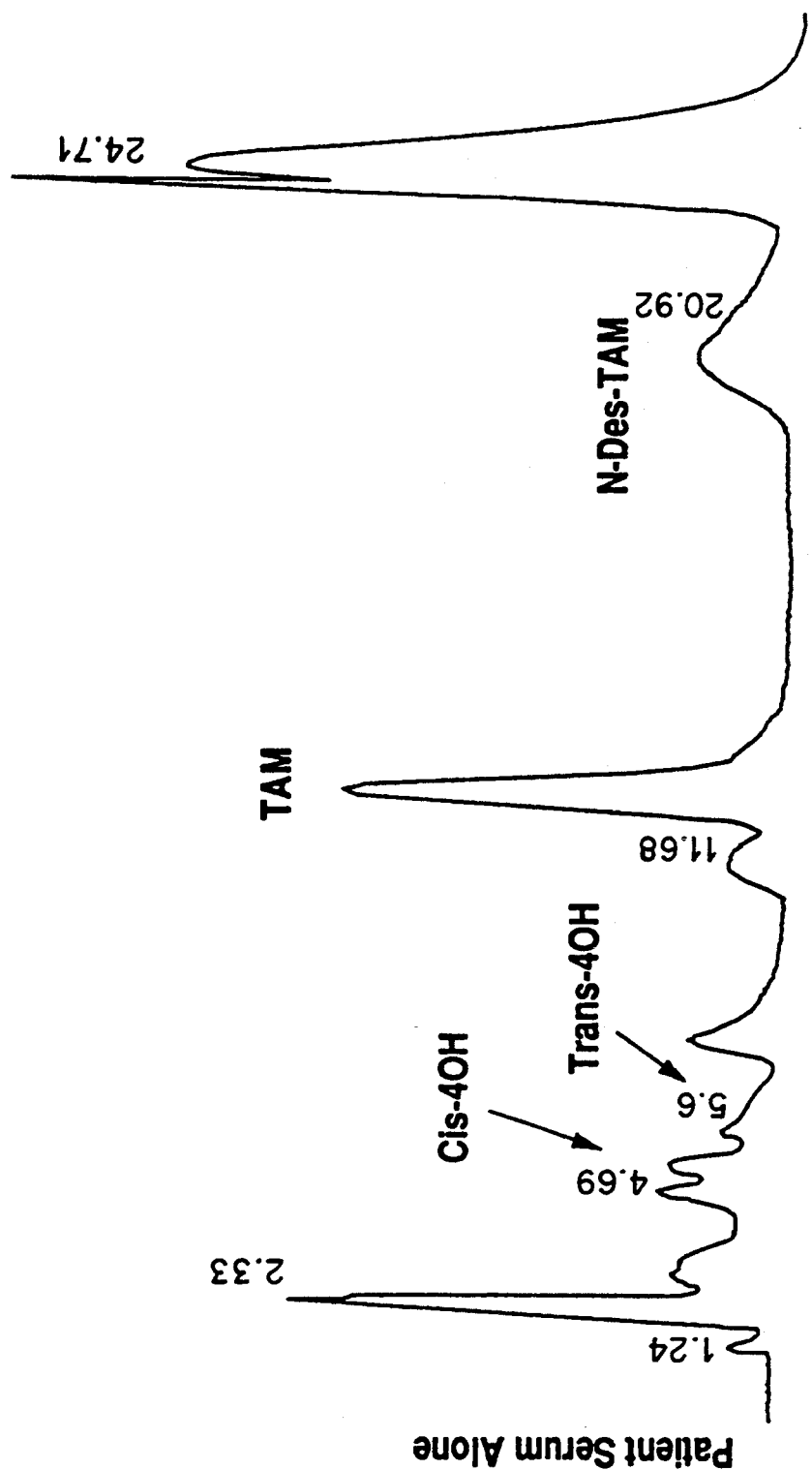
FIG. 9 shows example HPLC chromatographs demonstrating detection of tamoxifen, N-des-tamoxifen, and cis and trans 4-OH-TAM following treatment with 20 mg tamoxifen per day. These measurements demonstrate the capability to measure tamoxifen and its metabolites in serum.
Figure 9B:
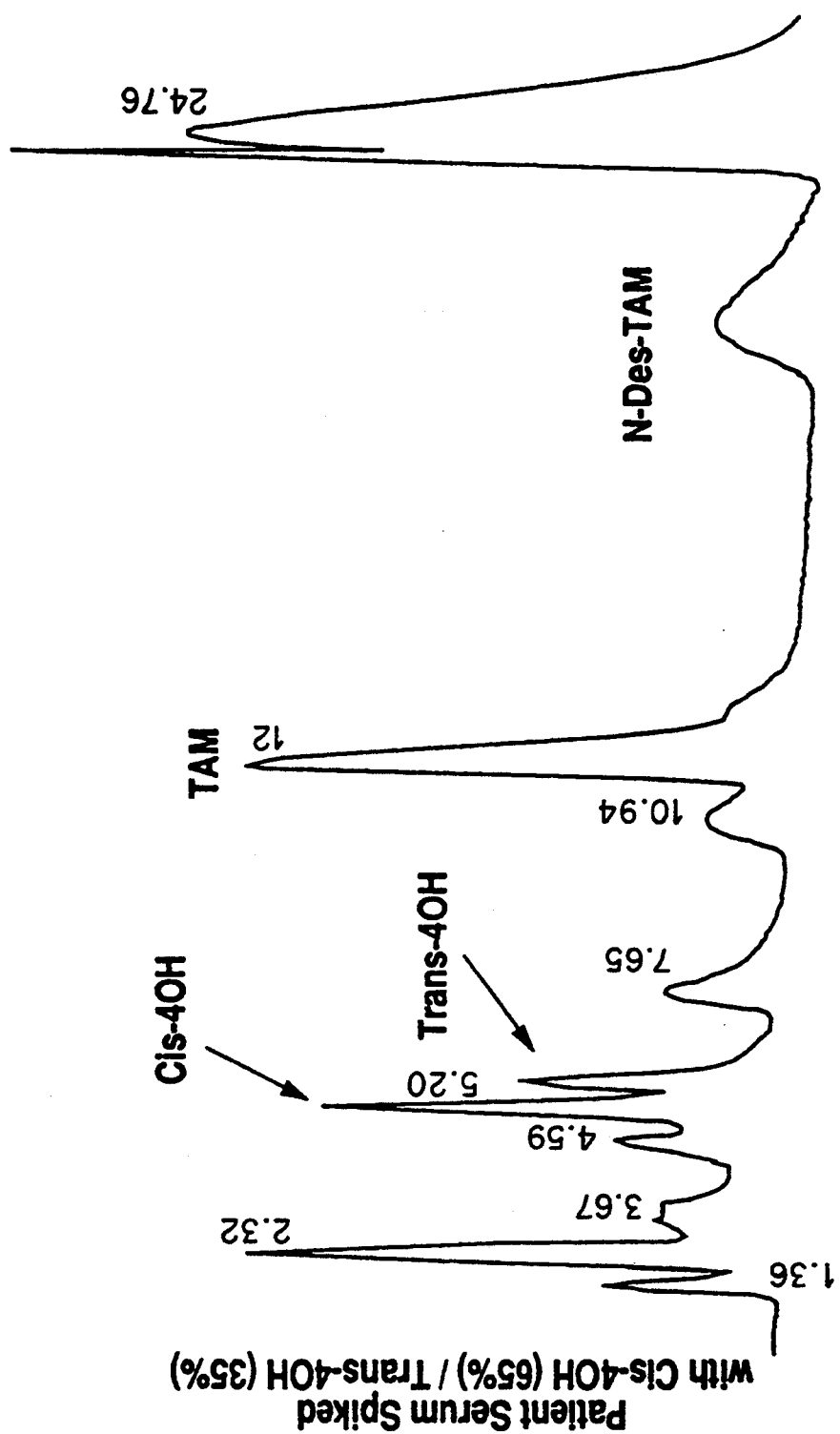

Because directly monitoring tumor drug levels in patients requires a biopsy for each reading, it may be impractical. Using a modified assay method, however, detection of tamoxifen, desmethyl-tamoxifen, and cis and trans 4-OH-TAM in serum is possible. FIG. 9 shows serum specimens following 20 mg daily doses of tamoxifen. Each serum specimen was spiked with cis and trans 4-OH-TAM reference standards which marked the appropriate peak in the unspiked sample. However, the relationship between plasma and tumor levels of the compounds of interest remains undetermined. Analogous results were obtained when a 160 mg tamoxifen dose was used. Metabolite E and bisphenol tamoxifen can also be detected in serum or plasma with this method. Measurement of the parent drug and its metabolites in peripheral blood leukocytes may increase sensitivity of the assay.

EXAMPLE 3

Indicative Tamoxifen Metabolites

MATERIALS AND METHODS

Figure 10A:
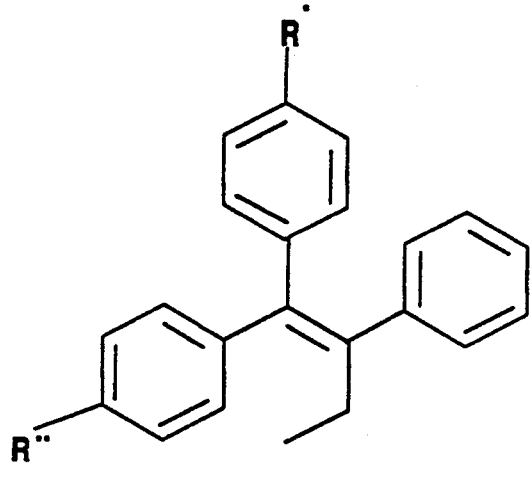
FIG. 10 shows structures of trans and cis tamoxifen isomers.
Trans-tamoxifen: $R' = -OCH_2CH_2N(CH_3)_2$, $R'' = -H$,
4-hydroxytamoxifen: $R' = -OCH_2CH_2N(CH_3)_2$, $R'' = -OH$,
N-desmethyltamoxifen: $R' = -OCH_2CH_2NH(CH_3)$, $R'' = -H$,
Bisphenol: $R' = -OH$, $R'' = -OH$,
Monophenol: $R' = -OH$, $R'' = -H$,
Metabolite Y: $R' = -CH_2CH_2OH$, $R'' = -H$,
Metabolite Z: $R' = -OCH_2CH_2NH_2$, $R'' = -H$
Metabolite $B_x$: $R'' = -OCH_2CH_2NHCH_3$, $R'' = -OH$,
cIS-TAMOXIFEN: $R' = -OCH_2CH_2N(CH_3)_2$, $R'' = -H$, 4-Hydroxytamoxifen; $R' = -OCH_2CH_2N(CH_3)_2$, $R'' = -OH$, monophenol; $R' = -OH$, $R'' = -H$.
Figure 10B:
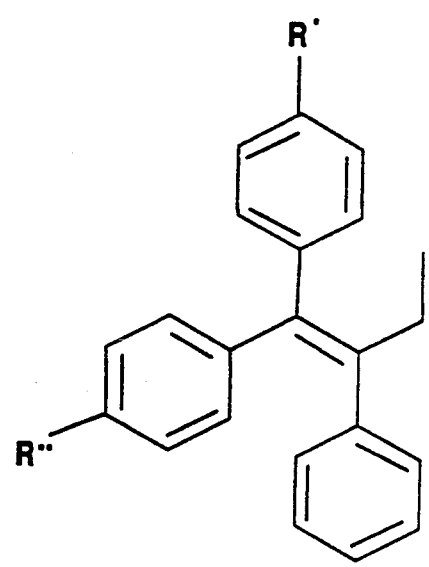

The chemical structures of trans- and cis-tamoxifen and tamoxifen metabolites are shown in FIG. 10. Tamoxifen citrate (ICI Pharma) and its metabolites (cis- & trans-4-hydroxytamoxifen, bis and monophenol tamoxifen) were generously provided by Professor Katzenellenbogen. All reagents were of HPLC grade including; methanol, hexane, 1-butanol (Fisher Scientific, Fair Lawn, N.J., and triethylamine (Sigma Chemical Co., St. Louis, Mo.).

Human breast tumors from various patients who failed tamoxifen therapy (20 mgs/day>one year) were obtained from the Breast Cancer Tumor Bank. A portion of the tumor was extracted, irradiated and analyzed by Mass Spectrometry (procedure described below). Tumor tissue was also obtained from an in vivo nude mouse model of acquired tamoxifen resistance. MCF-7 human breast tumors were harvested from nude mice after the development of tamoxifen resistance (4-6 months of tamoxifen administration, 500 ug/day). These tissues were frozen at $-20°$ C. until analysis. Frozen tissue samples were weighed, homogenized, and extracted. Briefly, all samples were extracted with 6.0 ml of 2% butanol in hexane, vortexed for 1.0 min, and then centrifuged for 10 min at $1000 \times g$. The organic phase was dried under $N_2$ gas at $37°$ C. and reconstituted in 200 $\mu l$ methanol prior to injection. The reconstituted samples were transferred to a Infrasil quartz cuvette (Fisher Scientific), irradiated for one minute with a 15 W Hg vapor lamp and injected onto a HPLC column.

The HPLC system consisted of a Beckman model 320 gradient liquid chromatograph, two model 110A pumps, and a model 420 controller. The HPLC was equipped with a reverse phase Altex C18 ultrasphere ODS column and a 100 $\mu l$ injection loop. The mobil phase consisted of 7% $H_2O$ and 0.18% triethylamine in methanol. The flow rate of the mobil phase was set at 0.5 ml/min. The fluorescence of photochemically activated compounds was detected with an Applied Biosystems 980 fluorometer with excitation wavelength set at 266 nm. Retention times and peak heights were recorded with a Spectraphysics 4100 integrator.

Non-irradiated samples were also injected onto the HPLC column and fractions were collected every minute. Fractionations corresponding to the retention times noted for the bisphenol and monophenol tamoxifen were further evaluated using mass-Spectrometry. The mass spectrometric behavior of the mono and bis phenols under electron impact ionization mass-spectrometry (EI-MS) was utilized. HPLC separated samples, in glass vials, were extracted with methanol, injected into glass capillaries and dried. Samples were introduced via a direct insertion probe. Spectra were recorded at 70 eV over the mass range of 70-500 at 10 seconds per decade with a resolution of 1000. The probe was heated in stages to $200°$ C.

Figure 11A:
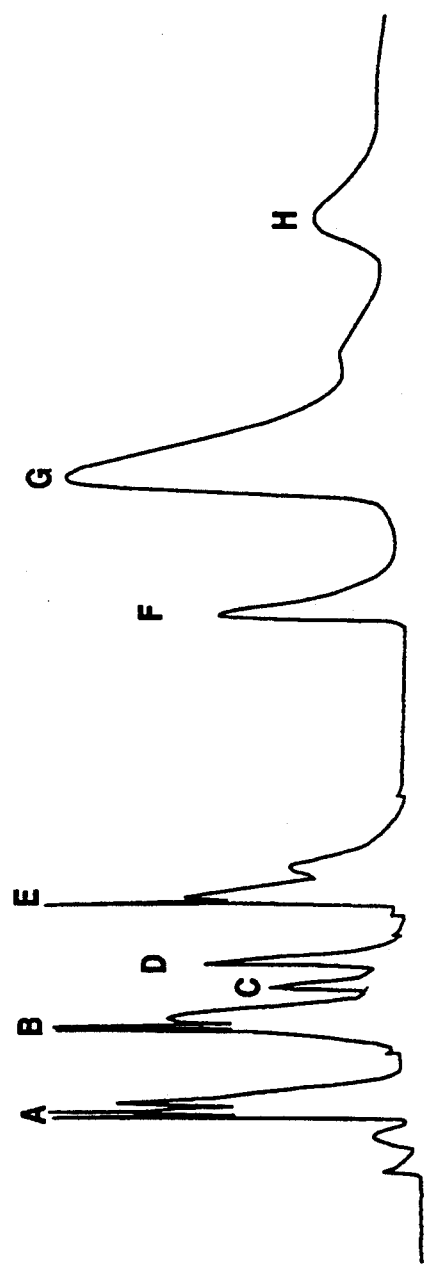
FIG. 11 shows separation of tamoxifen and metabolites in a spiked plasma sample (FIG. 11A) and in a tamoxifen resistant human breast tumor (FIG. 11B). Peaks in order are; bisphenol (a), monophenol (b), cis 4-hydroxytamoxifen (c), trans 4-hydroxytamoxifen (d), metabolite Bx (e), tamoxifen (f), metabolite Z (g) and N-desmethyltamoxifen (h).
Figure 11B:
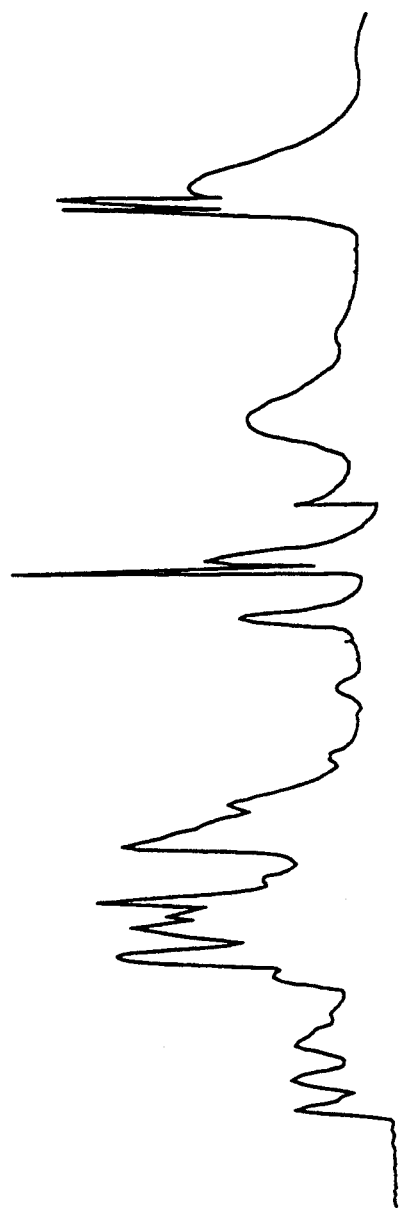

HPLC analysis of a human breast cancer tissue specimen and a spiked plasma sample is shown in FIG. 11. In the human breast cancer biopsy specimen, peaks corresponding to the retention times of bisphenol, monophenol, cis-4-hydroxy, trans 4-hydroxy, metabolite Bx, tamoxifen, metabolite Z and N-desmethyltamoxifen were observed. Tamoxifen and its N-desmethyl metabolite were the most abundant compounds present (200-400 mg/gm). Peaks were also noted for metabolites Bx and Z, however, these were not quantified. Peaks corresponding to bisphenol, monophenol, cis 4-hydroxy, metabolite Y and trans 4-hydroxy tamoxifen were present in low concentrations (<50 ng/gm), but due to the close proximity of their retention times absolute identification of these peaks required mass spectrometry analysis.

Figure 12:
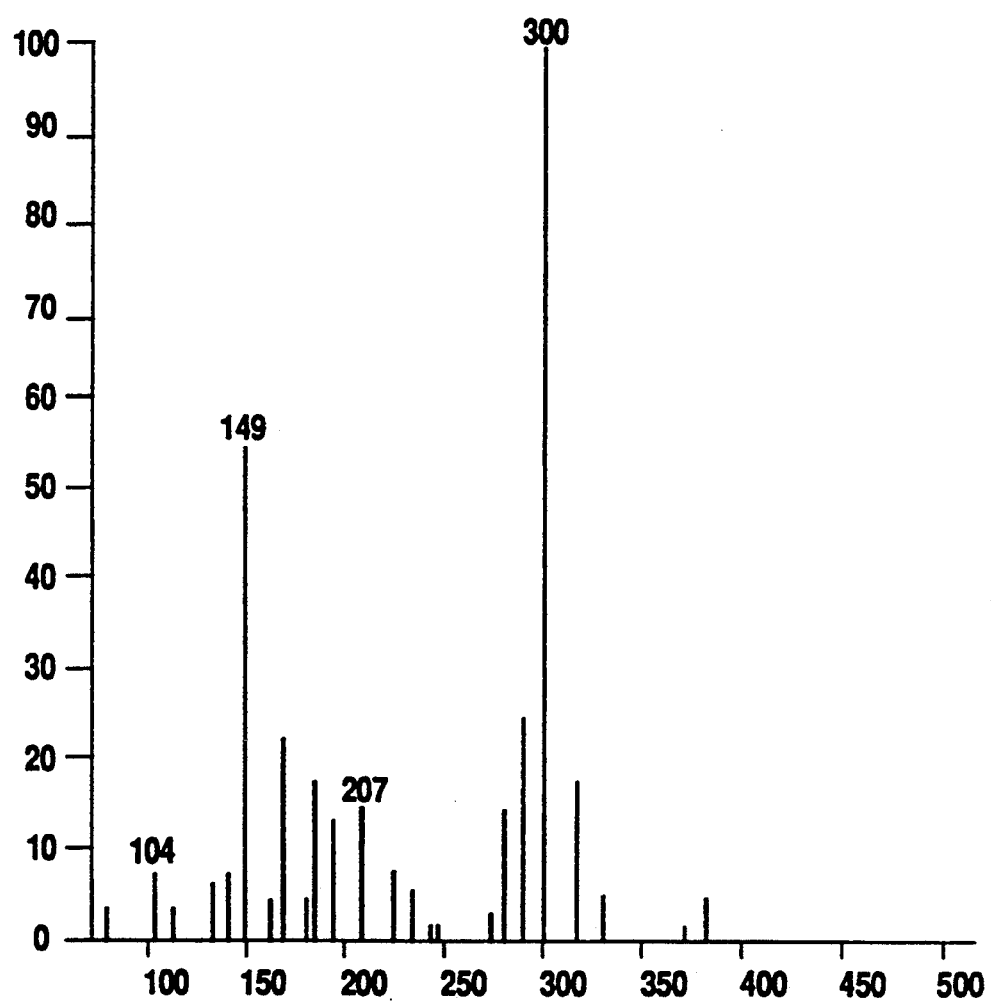
FIG. 12 shows electron-ionization (+) mass-spectrometric result of a peak isolated by HPLC fractionation of tamoxifen resistant human breast tumor (retention time=11–12 min). The peak at 300 m/z confirms the presence of monophenol tamoxifen (MW=300).

Further confirmation of the bisphenol and monophenol HPLC fractionations were done with mass spectrometry. Mass spectrometry analysis confirmed the presence of monophenol (FIG. 12). The HPLC peak at 11-12 minutes corresponded to a peak at m/z 300, consistent with the molecular weight of monophenol tamoxifen metabolite. In addition to the peak at m/z 300 (the monophenol), a strong peak at 149 m/z was observed. This was probably derived from phthlate ester impurities in the sample. Although a small but clear peak co-migrates with bisphenol on HPLC, the relative abundance of smaller weight compounds (<150) obscured the mass spectra analysis of these peaks. Therefore, the presence of bisphenol could not be confirmed in this study.

Results from HPLC analysis of MCF-7 tumors isolated from mice following tamoxifen administration are shown in FIG. (13). The top chromatogram shows results of the MCF-7 tumor analysis while the bottom shows a 25 ng/ml plasma sample spiked with bisphenol (A), monophenol (B), cis 4-hydroxy (C), trans 4-hydroxy (D), tamoxifen (E), and N-desmethytamoxifen (F). Peaks with retention times corresponding to monophenol, cis 4-hydroxy, trans 4-hydroxy, tamoxifen and N-desmethyltamoxifen were noted in the MCF-7 tamoxifen resistant mouse tumor. Metabolite Bx was also noted on the chromatogram (RT=17-19 min) but was not quantified. N-desmethylation and hydroxylation were the primary metabolic routes noted. Concentrations of tamoxifen and its metabolites were as follows: tamoxifen=3,255.9 ng/gm, N-desmethyltamoxifen=135.4 ng/gm cis 4-hydroxytamoxifen=42 ng/gm and trans 4-hydroxytamoxifen=36 ng/gm. Similar to the results noted in the human tumor specimen, the MCF-7 tumor also had peaks corresponding to monophenol (22 ng/gm). A very small peak was evident at a retention time similar to bisphenol.

In Table 5, levels of tamoxifen and a variety of tamoxifen metabolites are shown for tamoxifen-sensitive and tamoxifen-resistant tumors.

TABLE 5

Sensitive and Resistant MCF-7 Mouse Tumors: Tamoxifen and Metabolite Concentrations (ηg/g tissue)

| Sensitive Tumors: Animal # | TAM | N-DES | Cis 4-OH | Trans 4-OH | Mono-phenol | Bis-phenol |
|---|---|---|---|---|---|---|
| 1 | 3951.20 | 124.70 | 87.67 | 99.91 | 7.69 | — |
| 4 | 26926.12 | 331.82 | 139.89 | 337.58 | 109.07 | 44.27 |
| 7 | 26304.72 | 534.62 | 122.59 | 244.61 | 160.99 | 33.90 |
| 8 | 2339.52 | 5.95 | 70.83 | 71.01 | 37.72 | 39.80 |
| 13 | 20104.46 | 322.99 | 132.13 | 117.44 | 265.25 | 1491.44 |
| 15 | 15057.24 | 359.67 | 71.26 | 105.23 | 137.93 | 352.76 |
| N | 6 | 6 | 6 | 6 | 6 | 5 |
| X | 15780.54 | 279.95 | 104.06 | 162.63 | 119.78 | 392.43 |
| SD | 10721.90 | 187.05 | 31.19 | 104.87 | 92.31 | 629.19 |
| range | 2339.52–26926.12 | 5.95–534.62 | 70.83–139.89 | 71.01–337.58 | 7.69–265.25 | 33.90–1491.44 |
| 3 | 250.46 | 19.65 | 28.01 | 22.50 | — | 15.12 |

TABLE 5-continued

Sensitive and Resistant MCF-7 Mouse Tumors:
Tamoxifen and Metabolite Concentrations (ηg/g tissue)

Sensitive Tumors:

| Animal # | TAM | N-DES | Cis 4-OH | Trans 4-OH | Mono-phenol | Bis-phenol |
|---|---|---|---|---|---|---|
| 5 | 709.92 | 68.12 | 89.59 | 79.78 | 24.30 | 18.34 |
| 6 | 400.13 | 38.44 | 43.33 | 35.04 | 9.63 | 4.26 |
| 9 | 3255.87 | 135.44 | 42.32 | 35.46 | 21.99 | 3.93 |
| 10 | 402.59 | 50.27 | 55.37 | 47.55 | — | 32.75 |
| 11 | 710.41 | 65.70 | 51.94 | 53.08 | 20.66 | 9.77 |
| 12 | 310.19 | — | 45.04 | 31.66 | 232.66 | 43.87 |
| 14 | 775.66 | 127.29 | 103.44 | 97.52 | 47.82 | 52.72 |
| 16 | 2836.88 | 100.43 | 78.46 | 59.73 | 27.13 | 23.38 |
| N | 10 | 9 | 10 | 10 | 8 | 10 |
| X | 998.40 | 71.28 | 58.36 | 49.91 | 49.35 | 21.33 |
| SD | 1099.60 | 41.17 | 24.03 | 23.47 | 75.00 | 16.84 |
| range | 250.46–3255.87 | 19.65–135.44 | 28.01–103.44 | 22.50–97.52 | 9.63–232.66 | 3.93–52.72 |

From the data in Table 5 it should be noted that the tamoxifen/tamoxifen monophenol ratio (TAM/monophenol) is about 132 in tamoxifen-sensitive tumors and about 20 in tamoxifen-resistant tumors. The proportion of this estrogenic tamoxifen metabolite level to total TAM level shows a major increase in resistant tumors.

In patients receiving tamoxifen therapy, acquired resistance to tamoxifen generally occurs after six months. Several mechanisms of resistance have been suggested including hormone independence and altered metabolic pathways (Jordan). The present example documents that an estrogenic metabolite, monophenol-tamoxifen, is present in tumors isolated from patients who failed tamoxifen therapy. In addition, bisphenol-tamoxifen, a potent estrogenic metabolite, is also present in these patients. These metabolites are, for example, detected in human breast tumor tissue as well as in MCF-7 tumors isolated from mice.

The identification of estrogenic metabolites in tissues following long-term tamoxifen administration has important clinical ramifications. Both bisphenol and monophenol tamoxifen have documented estrogenic activity in vitro and in vivo. Metabolite E (monophenol) is also known to exit in isomeric form. Isomerization of transmetabolite E to cis metabolite E has been demonstrated in vitro (Murphy, 1990). The structure activity relationship of these isomers has also been examined. Trans-metabolite E appears to be a weak partial agonist, while the cis isomer is a potent estrogen agonist (Murphy, 1990). The cis form of metabolite E has also been shown to be more potent than bisphenol in stimulating T47D human breast cell growth (Murphy 1990). Using GC-MS, Fromson et al. identified metabolite E in the bile fluid of dogs where it accounted for approximately 6% of the radiolabeled compounds present in bile (Fromson 1973). Murphy et al. tentatively identified the presence of cis-metabolite E using GC-MS in the plasma of patients receiving tamoxifen (Murphy 1987). They report that cis-metabolite E was present in low concentration (0.9-2.0 ng/ml) in patients given tamoxifen for 14 days, while concentrations of 2.8 and 7.0 ng/ml were reported in two chronically (>2 yrs) treated patients (Murphy 1987).

REFERENCES

Furr B. J. A. and Jordan V. C. (1984), "The Pharmacology and Clinical Uses of Tamoxifen," Pharmacol Ther., 25:127.

Ferrazzi et al. (1977), "Oestrogen-like effect of tamoxifen on vaginal epithelium," Br. Med. J., 1:1351.

Adam et al. (1979), "The metabolism of tamoxifen in humans," Biochem Pharmacol. 27:145.

Kemp et al. (1983), "Identification and biological activity of tamoxifen metabolites in human serum," Biochem. Pharmacol., 32:2045.

Jordan et al. (1983) "Determination and pharmacology of a new hydroxylated metabolite of tamoxifen observed in patient sera during therapy for advanced breast cancer," Cancer Res., 43:1446

Lyman et al. (1985), "Metabolism of tamoxifen and its uterotrophic activity," Biochem Pharmacol, 34:2787.

Fromson et al. (1973), "The metabolism of tamoxifen (ICI 46,474). I. in laboratory animals," Xenobiotica, 3:693.

Sutherland et al. (1982), "Mechanisms of oestrogen antagonism by nonsteroidal antiestrogens," Molec. Cell Endocr., 25:5–23.

Osborne et al., "Acquired tamoxifen resistance correlates with reduced tuor tamoxifen and trans- 4hydroxytamoxifen in human breast cancer," JNCI, 1990 (in press).

Coezy et al. (1982), "Tamoxifen and metabolites in MCF-7 cells: correlation between binding to estrogen receptor and inhibition of cell growth," Cancer Res., 42:317–323.

Jordan et al. (1985), "Structure requirements for the pharmacological activity of nonsteroidal antiestrogens in vitro," Mol Pharmacol., 26:272–278.

Murphy et al. (1990), "Structure-Function relationships of hydroxylated metabolites of tamoxifen that control the proliferation of estrogen-response T47D breast cancer cells in vitro," Molec. Pharm., 38:737–744.

Murphy et al. (1987), "Analysis of tamoxifen and its metabolites in human plasma by gas chromatography mass spectrometry (GC-MS) using selected ion monitoring (SLM)," J. Steroid Biochem., 26:547–555.

Changes may be made in the construction, operation and arrangement of the various parts, elements, steps and procedures described herein without departing from the concept and scope of the invention as defined in the following claims. For example, it is understood that many methods for measuring tamoxifen isomers and metabolites may be used. Additionally after ratios, particularly those reflecting relative increases in estrogenic tamoxifen isomers and metabolites as compared to antiestrogenic analogs are equivalent. Of course these measurements and ratios may be found in body fluids where tamoxifen metabolites congregate, e.g., biopsy specimens, lymph fluid, blood or even urine.

We claim:

1. A method for detecting in vivo development of tamoxifen-resistant breast tumors in a patient being subjected to a course of tamoxifen treatment comprising:
    determining ratios of cis-4-hydroxy-tamoxifen concentration to trans-4-hydroxy-tamoxifen concentration in a fluid from said patient; and
    following said ratios during the course of tamoxifen treatment to determine onset of treatment resistance as characterized by an increase in the ratio of cis-4-hydroxy-tamoxifen concentration to trans-4-hydroxy-tamoxifen concentration as compared to said ratio expected for tumors sensitive to tamoxifen treatment.

2. The method according to claim 1 wherein said fluid is from breast tumor tissue.

3. The method according to claim 1 wherein said fluid is blood leukocytes.

4. The method according to claim 1 wherein said fluid is blood serum.

5. The method according to claim i wherein said fluid is blood plasma.

6. A method for detecting development of tamoxifen-resistant breast tumors in a breast cancer patient being subjected to a course of tamoxifen treatment comprising:
   determining tamoxifen concentration in fluid or tumor samples from said patient; and
   following said concentration during the course of tamoxifen treatment to determine onset of treatment resistance as characterized by a decrease in said tamoxifen concentration as compared to said concentration expected for tumors sensitive to tamoxifen treatment.

7. A method for detecting development of tamoxifen-resistant breast tumors in a breast cancer patient being subjected to a course of tamoxifen treatment, the method comprising:
   determining tamoxifen concentration and a ratio of cis-4-hydroxy-tamoxifen concentration to trans-4-hydroxy-tamoxifen concentration in a sample of fluid or breast-tumor from said patient; and
   following said tamoxifen concentration and ratio during the course of tamoxifen treatment to determine onset of treatment resistance as characterized by a decrease in tamoxifen concentration as compared to said concentration expected for tumors sensitive to tamoxifen treatment and an increase in the ratio of cis-4-hydroxy-tamoxifen concentration to trans-4-hydroxy-tamoxifen concentration as compared to said ratio expected for tumors sensitive to tamoxifen treatment.

8. A method for detecting development of resistance to treatment by a trans triphenylethylene antiestrogen in a breast cancer patient being subjected to a course of treatment with a trans triphenylethylene antiestrogen, the method comprising:
   determining tissue ratios of cis triphenylethylene antiestrogen isomer to trans triphenylethylene antiestrogen isomer in fluid or tissue from said patient; and
   following said ratio during the course of treatment to determine onset of treatment resistance as characterized by an increase in the ratio as compared to said ratio expected for tumors sensitive to tamoxifen treatment.

9. The method according to claim 8 wherein said tissue is breast tumor tissue.

10. The method according to claim 8 wherein said tissue is blood leukocytes.

11. The method according to claim 8 wherein said tissue is blood serum.

12. The method according to claim 8 wherein said tissue is blood plasma.

13. The method according to claims 1, 7 or 8 wherein said determining step comprises photoactivation of a tissue sample extract.

14. The method of claim 13 wherein the photoactivation involves irradiation with ultraviolet light.

15. The method of claims 1, 7 or 8 wherein the determining step comprises high performance liquid chromatography.

16. A method for detecting the onset of tumor tamoxifen resistance in a breast cancer patient being subjected to a course of tamoxifen treatment, the method comprising, during the course of said treatment:
   (a) determining a level of tamoxifen, an antiestrogenic tamoxifen isomer or an antiestrogenic tamoxifen metabolite in a tissue or fluid sample from said patient;
   (b) determining a level of an estrogenic tamoxifen isomer or an estrogenic tamoxifen metabolite in a tissue or fluid sample from said patient; and
   (c) detecting onset of tumor tamoxifen resistance when the level determined in step (b) increases relative to the level determined in step (a) as compared to the levels expected for tumors sensitive to tamoxifen treatment.

17. The method of claim 16 where a level of antiestrogenic tamoxifen isomer is determined in step (a) and a level of estrogenic tamoxifen isomer is determined in step (b).

18. The method of claim 16 where a level of tamoxifen is determined in step (a) and a level of an estrogenic tamoxifen metabolite is determined in step (b).

19. The method of claim 18 where a level of tamoxifen is determined in step (a) and a level of tamoxifen monophenol is determined in step (b).

20. The method of claim 16 wherein the estrogenic tamoxifen metabolite is tamoxifen monophenol.

21. The method of claim 16 wherein the estrogenic tamoxifen metabolite is tamoxifen bisphenol.

* * * * *